US011439390B2

(12) United States Patent
Patel et al.

(10) Patent No.: US 11,439,390 B2
(45) Date of Patent: Sep. 13, 2022

(54) SURGICAL INSTRUMENT WITH LOCKOUT MECHANISM

(71) Applicant: INTUITIVE SURGICAL OPERATIONS, INC., Sunnyvale, CA (US)

(72) Inventors: Atal C Patel, Mission Viejo, CA (US); Matthew Aaron Wixey, San Jose, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 0 days.

(21) Appl. No.: 16/969,483

(22) PCT Filed: Feb. 26, 2019

(86) PCT No.: PCT/US2019/019501
§ 371 (c)(1),
(2) Date: Aug. 12, 2020

(87) PCT Pub. No.: WO2019/165403
PCT Pub. Date: Aug. 29, 2019

(65) Prior Publication Data
US 2020/0397430 A1 Dec. 24, 2020

Related U.S. Application Data

(60) Provisional application No. 62/635,348, filed on Feb. 26, 2018.

(51) Int. Cl.
*A61B 17/068* (2006.01)
*A61B 17/072* (2006.01)

(52) U.S. Cl.
CPC ........ *A61B 17/0686* (2013.01); *A61B 17/072* (2013.01); *A61B 2017/07264* (2013.01);
(Continued)

(58) Field of Classification Search
CPC .............. A61B 17/068; A61B 17/0684; A61B 17/0686; A61B 17/072; A61B 17/07207;
(Continued)

(56) References Cited

U.S. PATENT DOCUMENTS

| 4,305,539 A | 12/1981 | Korolkov et al. |
| 4,319,576 A | 3/1982 | Rothfuss |

(Continued)

FOREIGN PATENT DOCUMENTS

| EP | 1090592 A1 | 4/2001 |
| EP | 1728473 A1 | 12/2006 |

(Continued)

OTHER PUBLICATIONS

United States Patent Office; International Search Report & Written Opinion; dated May 9, 2019; PCT Application No. PCT/US19/19501.

(Continued)

*Primary Examiner* — Stephen F. Gerrity
*Assistant Examiner* — Linda J Hodge
(74) *Attorney, Agent, or Firm* — Farber LLC

(57) ABSTRACT

Locking assemblies for surgical clamping and cutting instruments include a locking member and a switch. A drive member may be configured to releasably engage a knife and/or a shuttle of the surgical instrument for translating the knife and/or shuttle in a distal direction through a firing stroke. The locking member is movable from a first position permitting distal translation of the drive member through the firing stroke, and a second position inhibiting distal translation of the drive member through the firing stroke. A switch, when proximally positioned, releasably engages the locking member to maintain the locking member in the first position. The switch disengages from the locking member when the switch is moved to a distal position.

20 Claims, 30 Drawing Sheets

(52) U.S. Cl.
CPC .............. *A61B 2017/07271* (2013.01); *A61B 2017/07278* (2013.01); *A61B 2017/07285* (2013.01)

(58) Field of Classification Search
CPC ........... A61B 2017/07264; A61B 2017/07271; A61B 2017/07278; A61B 2017/07285; A61B 2017/2933; A61B 2090/0814
USPC ................................. 227/175.2, 175.3, 175.4
See application file for complete search history.

(56) References Cited

U.S. PATENT DOCUMENTS

| | | |
|---|---|---|
| 4,429,695 A | 2/1984 | Green |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,571,116 A | 11/1996 | Bolanos et al. |
| 5,571,285 A | 11/1996 | Chow et al. |
| 5,615,820 A | 4/1997 | Viola |
| 5,624,452 A | 4/1997 | Yates |
| 5,628,446 A | 5/1997 | Geiste et al. |
| 5,667,626 A | 9/1997 | Cayford et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,709,680 A | 1/1998 | Yates et al. |
| 5,752,644 A | 5/1998 | Bolanos et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,079,606 A | 6/2000 | Milliman et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,503,259 B2 | 1/2003 | Huxel et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,365,972 B2 | 2/2013 | Aranyi et al. |
| 8,371,492 B2 | 2/2013 | Aranyi et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,939 B2 | 3/2014 | Garrison |
| 8,783,541 B2 | 7/2014 | Shelton, IV et al. |
| 8,800,841 B2 | 8/2014 | Ellerhorst et al. |
| 8,858,547 B2 | 10/2014 | Brogna |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,192,378 B2 | 11/2015 | Aranyi et al. |
| 9,192,379 B2 | 11/2015 | Aranyi et al. |
| 9,216,019 B2 | 12/2015 | Schmid et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |

(56) References Cited

U.S. PATENT DOCUMENTS

| | | | |
|---|---|---|---|
| 10,111,659 | B2 | 10/2018 | Racenet et al. |
| 10,231,732 | B1 | 3/2019 | Racenet et al. |
| 10,285,693 | B2 | 5/2019 | Kimsey et al. |
| 10,646,219 | B2 | 5/2020 | Racenet et al. |
| 10,828,027 | B2 | 11/2020 | Racenet et al. |
| 10,863,988 | B2 | 12/2020 | Patel et al. |
| 2002/0165562 | A1 | 11/2002 | Grant et al. |
| 2004/0232199 | A1 | 11/2004 | Shelton et al. |
| 2004/0267310 | A1 | 12/2004 | Racenet et al. |
| 2005/0006430 | A1 | 1/2005 | Wales |
| 2005/0006434 | A1 | 1/2005 | Wales et al. |
| 2005/0070925 | A1 | 3/2005 | Shelton, IV et al. |
| 2005/0070958 | A1 | 3/2005 | Swayze et al. |
| 2005/0173490 | A1 | 8/2005 | Shelton, IV |
| 2005/0178813 | A1 | 8/2005 | Swayze et al. |
| 2005/0187576 | A1 | 8/2005 | Whitman et al. |
| 2006/0000868 | A1 | 1/2006 | Shelton, IV et al. |
| 2006/0016853 | A1 | 1/2006 | Racenet |
| 2006/0022014 | A1 | 2/2006 | Shelton, IV et al. |
| 2006/0022015 | A1 | 2/2006 | Shelton, IV et al. |
| 2006/0024817 | A1 | 2/2006 | Deguchi et al. |
| 2006/0025809 | A1 | 2/2006 | Shelton, IV |
| 2006/0025810 | A1 | 2/2006 | Shelton, IV |
| 2006/0025811 | A1 | 2/2006 | Shelton, IV |
| 2006/0025812 | A1 | 2/2006 | Shelton, IV |
| 2006/0025813 | A1 | 2/2006 | Shelton et al. |
| 2006/0025816 | A1 | 2/2006 | Shelton, IV |
| 2006/0049230 | A1 | 3/2006 | Shelton, IV et al. |
| 2006/0097026 | A1 | 5/2006 | Shelton, IV |
| 2006/0190031 | A1 | 8/2006 | Wales et al. |
| 2006/0226196 | A1 | 10/2006 | Hueil et al. |
| 2007/0010838 | A1 | 1/2007 | Shelton, IV |
| 2007/0045379 | A1 | 3/2007 | Shelton, IV |
| 2007/0102475 | A1 | 5/2007 | Ortiz et al. |
| 2007/0262116 | A1 | 11/2007 | Hueil et al. |
| 2008/0023522 | A1 | 1/2008 | Olson et al. |
| 2008/0078804 | A1 | 4/2008 | Shelton et al. |
| 2009/0277947 | A1 | 11/2009 | Viola |
| 2010/0108740 | A1 | 5/2010 | Pastorelli et al. |
| 2011/0022078 | A1 | 1/2011 | Hinman |
| 2011/0174863 | A1 | 7/2011 | Shelton, IV et al. |
| 2011/0295270 | A1 | 12/2011 | Giordano et al. |
| 2012/0022584 | A1 | 1/2012 | Donnigan et al. |
| 2012/0223121 | A1 | 9/2012 | Viola et al. |
| 2013/0015231 | A1 | 1/2013 | Kostrzewski |
| 2013/0056521 | A1 | 3/2013 | Swensgard |
| 2013/0068821 | A1 | 3/2013 | Huitema et al. |
| 2013/0087599 | A1 | 4/2013 | Krumanaker et al. |
| 2013/0098965 | A1 | 4/2013 | Kostrzewski et al. |
| 2013/0148577 | A1 | 6/2013 | Terry et al. |
| 2013/0248577 | A1 | 9/2013 | Leimbach et al. |
| 2014/0001236 | A1 | 1/2014 | Shelton, IV et al. |
| 2014/0175152 | A1 | 6/2014 | Hess et al. |
| 2014/0263546 | A1* | 9/2014 | Aranyi ............ A61B 17/07207 227/175.2 |
| 2014/0263559 | A1 | 9/2014 | Williams et al. |
| 2014/0263567 | A1 | 9/2014 | Williams et al. |
| 2014/0263569 | A1 | 9/2014 | Williams et al. |
| 2015/0209037 | A1 | 7/2015 | Kostrzewski et al. |
| 2015/0250530 | A1 | 9/2015 | Manzo et al. |
| 2015/0272576 | A1* | 10/2015 | Cappola ............... A61B 17/072 227/175.2 |
| 2015/0297227 | A1 | 10/2015 | Huitema et al. |
| 2016/0038227 | A1 | 2/2016 | Garrison |
| 2016/0120544 | A1 | 5/2016 | Shelton, IV et al. |
| 2016/0175033 | A1 | 6/2016 | Le |
| 2016/0192999 | A1 | 7/2016 | Stulen et al. |
| 2016/0270780 | A1 | 9/2016 | Hall et al. |
| 2016/0287251 | A1 | 10/2016 | Shelton, IV et al. |
| 2017/0010578 | A1 | 1/2017 | Miyakawa |
| 2017/0042604 | A1 | 2/2017 | McFarland et al. |
| 2017/0079710 | A1 | 3/2017 | Deville et al. |
| 2017/0097035 | A1 | 4/2017 | Zimmerman et al. |
| 2017/0245857 | A1 | 8/2017 | Shelton, IV et al. |
| 2017/0296172 | A1 | 10/2017 | Harris et al. |
| 2018/0021042 | A1 | 1/2018 | Nicholas et al. |
| 2018/0161052 | A1 | 6/2018 | Weir et al. |
| 2018/0168581 | A1 | 6/2018 | Hunter et al. |
| 2018/0168622 | A1 | 6/2018 | Shelton, IV et al. |
| 2018/0168628 | A1* | 6/2018 | Hunter ............ A61B 17/07207 |
| 2018/0168641 | A1 | 6/2018 | Harris et al. |
| 2018/0168642 | A1 | 6/2018 | Shelton, IV et al. |
| 2018/0168649 | A1 | 6/2018 | Shelton, IV et al. |
| 2019/0142531 | A1 | 5/2019 | Wentworth et al. |
| 2019/0167266 | A1 | 6/2019 | Patel et al. |
| 2021/0177495 | A1 | 6/2021 | Ross et al. |
| 2021/0177500 | A1 | 6/2021 | Khalaji |

FOREIGN PATENT DOCUMENTS

| | | | |
|---|---|---|---|
| EP | 1479346 | B1 | 1/2007 |
| EP | 1621141 | B1 | 7/2007 |
| EP | 1316290 | B1 | 2/2012 |
| EP | 1754445 | B1 | 10/2013 |
| EP | 3135225 | A2 * | 3/2017 ........... A61B 17/068 |
| EP | 3173029 | A1 | 5/2017 |
| FR | 2828952 | B1 | 12/2005 |
| JP | 5301166 | B2 | 9/2013 |
| JP | 2016508792 | A | 3/2016 |
| JP | 2016513570 | A | 5/2016 |
| JP | 2017527396 | A | 9/2017 |
| JP | 6411461 | B2 | 10/2018 |
| JP | 2019141659 | A | 8/2019 |
| SU | 405234 | A1 | 9/1975 |
| SU | 886900 | A1 | 12/1981 |
| SU | 1333319 | A2 | 8/1987 |
| SU | 1442191 | A1 | 12/1988 |
| SU | 1459659 | A1 | 2/1989 |
| WO | WO-8602254 | A1 | 4/1986 |
| WO | WO-9005489 | A1 | 5/1990 |
| WO | WO-9734533 | A1 | 9/1997 |
| WO | WO-03094743 | A1 | 11/2003 |
| WO | WO-03094746 | A1 | 11/2003 |
| WO | WO-03094747 | A1 | 11/2003 |
| WO | WO-2012142872 | A1 | 10/2012 |
| WO | WO-2014106275 | A1 | 7/2014 |
| WO | WO-2017034803 | A2 | 3/2017 |
| WO | WO-2017156070 | A1 | 9/2017 |
| WO | WO-2017214243 | A1 | 12/2017 |
| WO | WO-2018005750 | A1 | 1/2018 |
| WO | WO-2018071497 | A1 | 4/2018 |
| WO | WO-2018118402 | A1 | 6/2018 |

OTHER PUBLICATIONS

International Preliminary Report on Patentability for Application No. PCT/US2019/017646, dated Aug. 27, 2020, 10 pages.
International Search Report and Written Opinion for Application No. PCT/US2020/025655, dated Jul. 22, 2020, 8 pages.
International Search Report and Written Opinion for Application No. PCT/US2020/054568, dated Jan. 29, 2021, 13 pages.
International Preliminary Report on Patentability for Application No. PCT/US2019/019501, dated Sep. 3, 2020, 7 pages.
International Search Report and Written Opinion for Application No. PCT/US19/17646, dated Apr. 16, 2019, 11 pages.
International Search Report and Written Opinion for Application No. PCT/US2019/056979, dated Dec. 18, 2019, 8 pages.
International Search Report and Written Opinion for Application No. PCT/US2019/062344, dated Mar. 23, 2020, 17 pages.
International Search Report and Written Opinion for Application No. PCT/US2019/062768, dated Mar. 9, 2020, 15 pages.
International Search Report and Written Opinion for Application No. PCT/US2019/064861, dated Mar. 30, 2020, 18 pages.
International Search Report and Written Opinion for Application No. PCT/US2019/066513, dated Apr. 21, 2020, 8 pages.
International Search Report and Written Opinion for Application No. PCT/US2019/066530, dated Apr. 21, 2020, 8 pages.
International Search Report and Written Opinion for Application No. PCT/US2020/020672, dated Jun. 29, 2020, 10 pages.
International Search Report and Written Opinion for Application No. PCT/US2020/033481, dated Sep. 3, 2020, 22 pages.

(56) References Cited

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

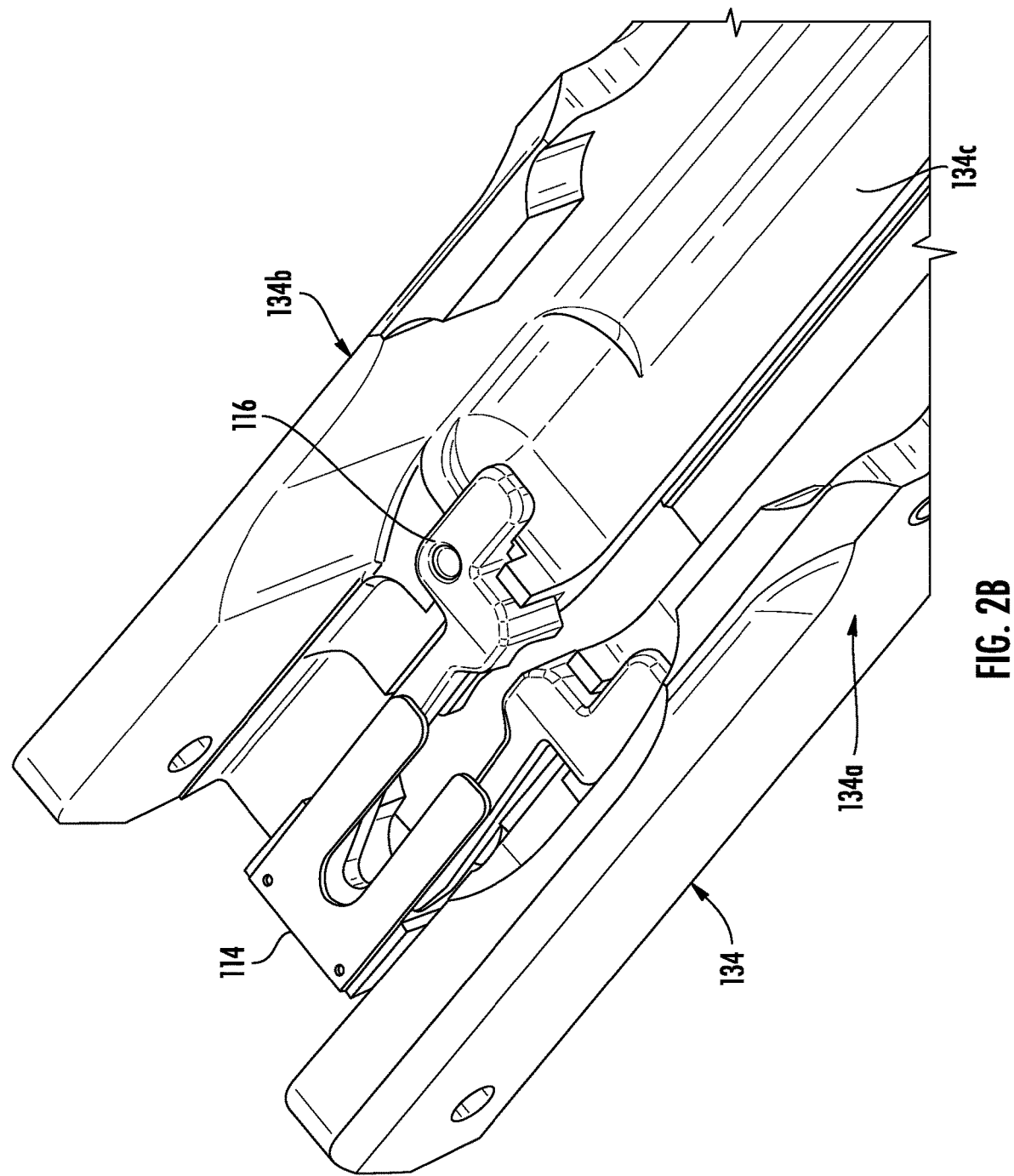

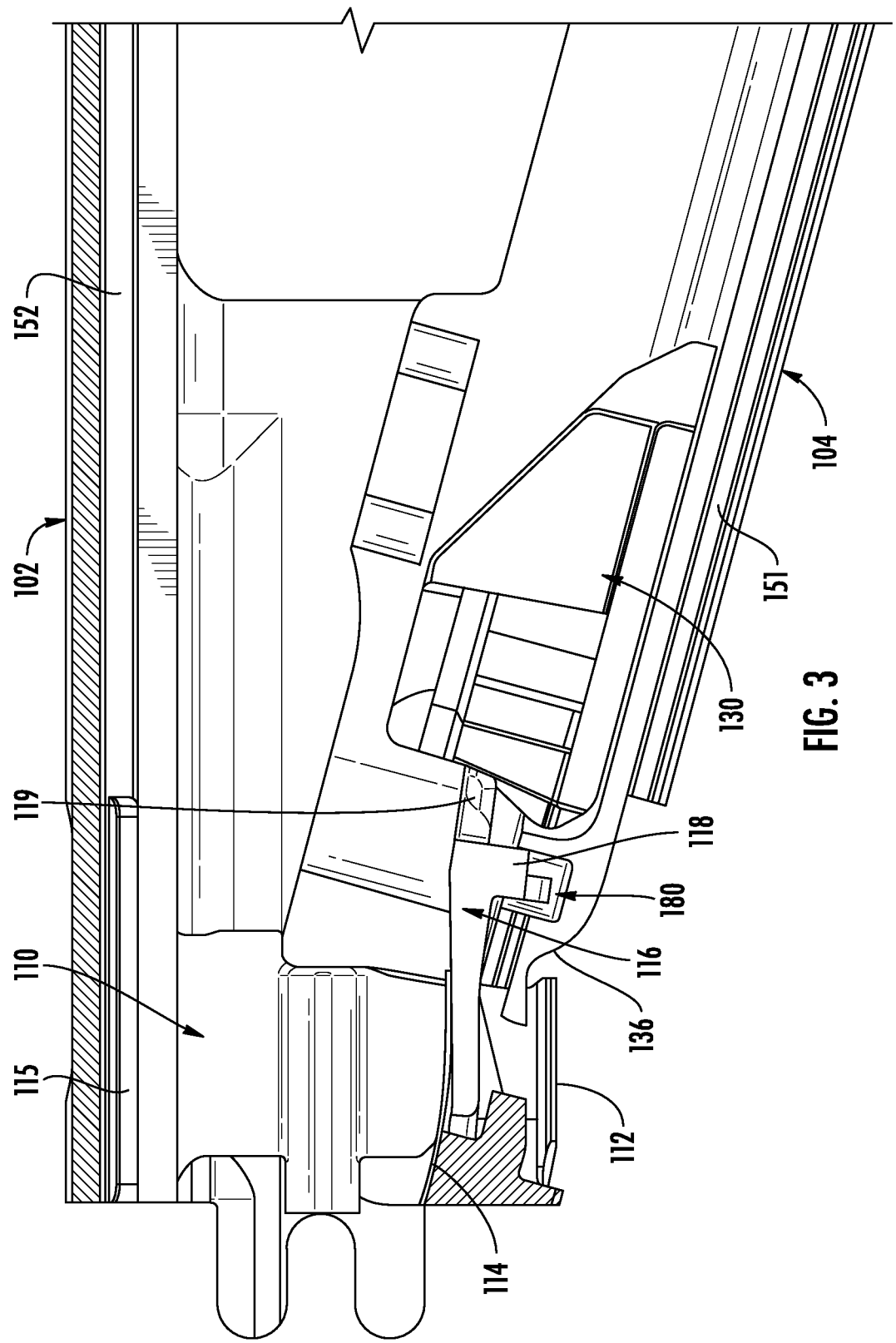

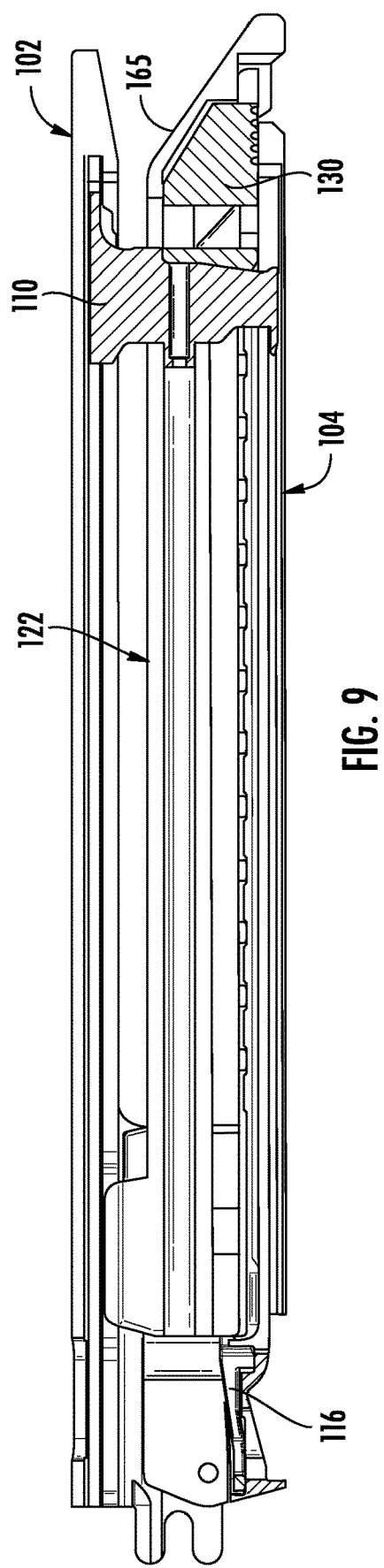

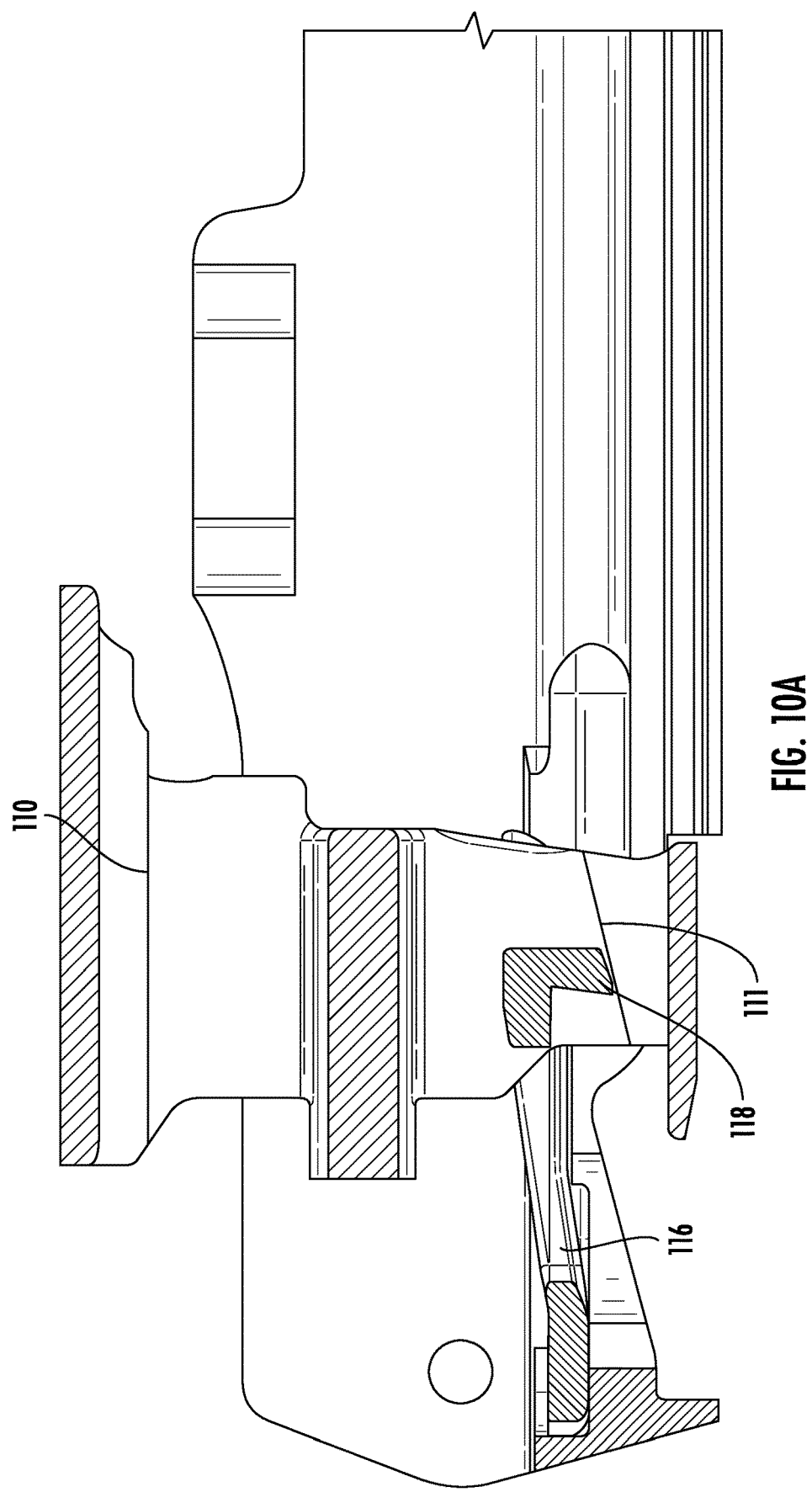

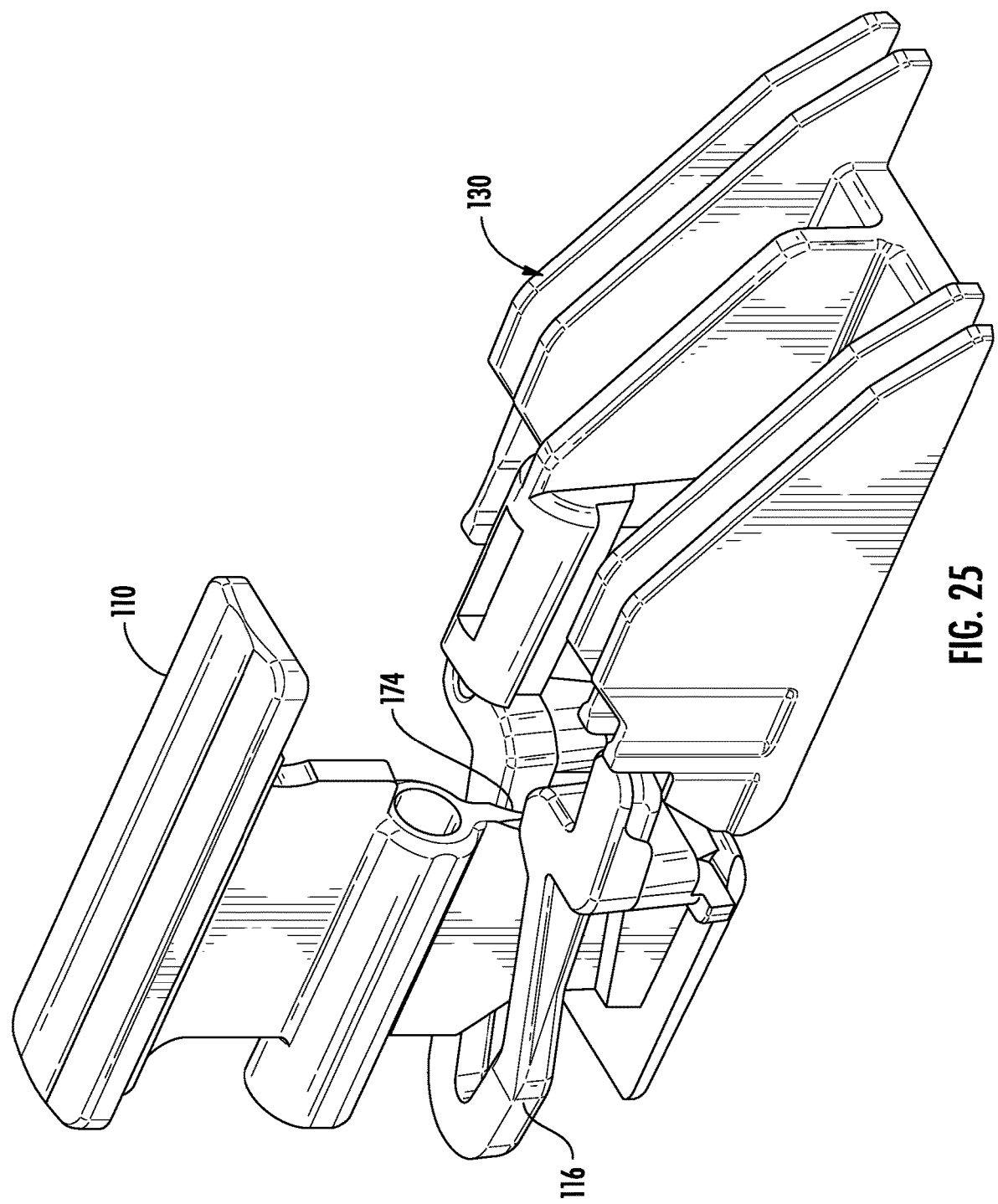

US 11,439,390 B2

SURGICAL INSTRUMENT WITH LOCKOUT MECHANISM

CROSS REFERENCE TO RELATED APPLICATIONS

This application is the National Stage of International Application No. PCT/US19/19501 filed Feb. 26, 2019 which claims benefit of U.S. Provisional Application No. 62/635,348 filed Feb. 26, 2018, the entirety of which is herein incorporated by reference.

TECHNICAL FIELD

The present disclosure relates to surgical stapling instruments having a locking mechanism to prevent actuation of a knife when there is a spent or previously fired cartridge in place.

BACKGROUND

Surgical clamping and cutting instruments, such as, for example, surgical stapling instruments, may include an end effector having opposing jaws that clamp tissue and a knife that cuts the clamped tissue. It is often advantageous for an end effector of a surgical stapling instrument to be reusable. To that end, staple cartridges can be fitted into one jaw of the end effector prior to each use of the surgical stapling instrument.

It is desirable to prevent firing of a surgical stapling instrument while a spent cartridge remains in place on the jaw. Thus, a need exists for effective mechanisms to prevent firing of a surgical stapling instrument while a spent staple cartridge is in place in the end effector of the surgical stapling instrument.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to surgical stapling instruments having a locking mechanism. Surgical stapling instruments described herein employ a locking mechanism to prevent actuation of a knife when there is a spent or previously fired cartridge in place.

In one aspect, a surgical stapling instrument in accordance with this disclosure includes an anvil jaw assembly and a staple jaw assembly. The staple jaw assembly includes a channel configured to receive a staple cartridge, the staple cartridge including a shuttle. The channel includes two side walls, a bottom wall, and a cam surface adjacent the bottom wall. The surgical stapling instrument further includes a drive member configured to releasably engage and translate the shuttle in a distal direction through a staple firing stroke. The locking member is pivotable between a first position permitting distal translation of the drive member, and a second position preventing distal translation of the drive member. The drive member further includes a footer configured to engage the cam surface and simultaneously pivot the channel, the shuttle, and the locking member towards the anvil assembly.

In another aspect, a surgical stapling instrument in accordance with this disclosure includes an anvil jaw assembly, a drive member configured to translate in a distal direction through a staple firing stroke, and a locking member pivotable between a first position permitting distal translation of the drive member, and a second position preventing distal translation of the drive member. The staple jaw assembly further includes a channel configured to receive a staple cartridge, the staple cartridge including a shuttle. The channel includes two sidewalls, each sidewall having a guide structure configured to direct a proximal ramped surface of the shuttle into contact with a distal ramped surface of the locking member to urge a portion of the locking member onto a shelf of the shuttle to maintain the locking member in the first position.

In another aspect, a surgical stapling instrument in accordance with this disclosure includes an anvil jaw assembly and a staple jaw assembly. The staple jaw assembly includes a channel configured to receive a staple cartridge, the staple cartridge including a shuttle. The channel includes two side walls and a bottom wall having a pair of openings. The surgical stapling instrument further includes a drive member configured to releasably engage and translate the shuttle in a distal direction through a staple firing stroke. A locking member is pivotable between a first position permitting distal translation of the drive member, and a second position preventing distal translation of the drive member. The locking member includes a pair of feet configured to pass through respective openings in the bottom wall of the channel. The pair of feet are movable from a first position preventing removal of the feet from the openings, to a second position allowing removal of the feet from the openings.

In another aspect a surgical instrument is provided, including an anvil assembly and a staple jaw assembly including a channel defining a longitudinal axis and configured to receive a staple cartridge. The staple cartridge includes a shuttle. A drive member is configured to releasably engage and translate the shuttle in a distal direction through a staple firing stroke. The surgical stapling instrument further includes a locking member pivotable between a first position permitting distal translation of the drive member, and a second position preventing distal translation of the drive member. The locking member includes a pair of distally extending arms, each arm having a proximally facing chamfered surface configured to engage and align the drive member along the longitudinal axis of the channel as the drive member translates distally between the arms of the locking member.

BRIEF DESCRIPTION OF THE DRAWINGS

The above and other aspects, features, and advantages of the present surgical stapling instruments having a locking mechanism will become more apparent in light of the following detailed description when taken in conjunction with the accompanying drawings in which:

FIG. 2B depicts a partial perspective view of the proximal end of the channel and locking member of FIG. 2A;

FIG. 3 is a partial cross-sectional view of the end effector of FIG. 1B in an open position;

FIG. 9 is a partial side, cross-sectional view of the end effector of FIG. 1B showing the drive member and shuttle advanced to the distal-most position;

FIG. 10A is a partial cross-sectional view showing the drive member interacting with the locking member upon retraction of the drive member;

FIG. 25 is a partial side view of the drive member in accordance with the embodiment of FIG. 24 engaging chamfered surfaces of the locking member while the locking member is in the unlocked position.

DETAILED DESCRIPTION

Particular embodiments of the present surgical stapling instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in unnecessary detail.

The present disclosure relates to surgical stapling instruments including a locking member and a drive member configured to engage at least one of a knife or a shuttle of a surgical stapling instrument and to translate the same in a distal direction through a staple firing stroke. Contact between the drive member and the knife and/or shuttle is releasable in that once the knife and/or shuttle are translated by the drive member in the distal direction through a staple firing stroke, the knife and/or shuttle disengages from the drive member, remains at a distal portion of the stapling instrument, and is not translated in a proximal direction by the drive member. The locking member is movable from a first position permitting distal translation of the drive member through the staple-firing stroke, and a second position inhibiting distal translation of the drive member through the staple firing stroke. A spring is configured to bias the locking member toward the second position. When the shuttle is in the proximal position, the shuttle releasably maintains the locking member in the first position. When the shuttle advances distally, the shuttle disengages from the locking member thereby allowing the locking member to move to the second position.

While the following disclosure is presented with respect to a linear surgical stapler where staples are sequentially fired, it should be understood that the present locking assemblies may be readily adapted for use in any type of surgical clamping and cutting instruments, whether or not the surgical clamping and cutting instrument applies a fastener. The surgical clamping and cutting instrument may be a minimally invasive (e.g., laparoscopic) instrument or an instrument used for open surgery.

Additionally, the present locking assemblies may be readily adapted for use in surgical instruments that are activated using any technique within the purview of those skilled in the art, such as, for example, manually activated surgical instruments, powered surgical instruments (e.g., electromechanically powered instruments), robotic surgical instruments, and the like.

Figure 1A:
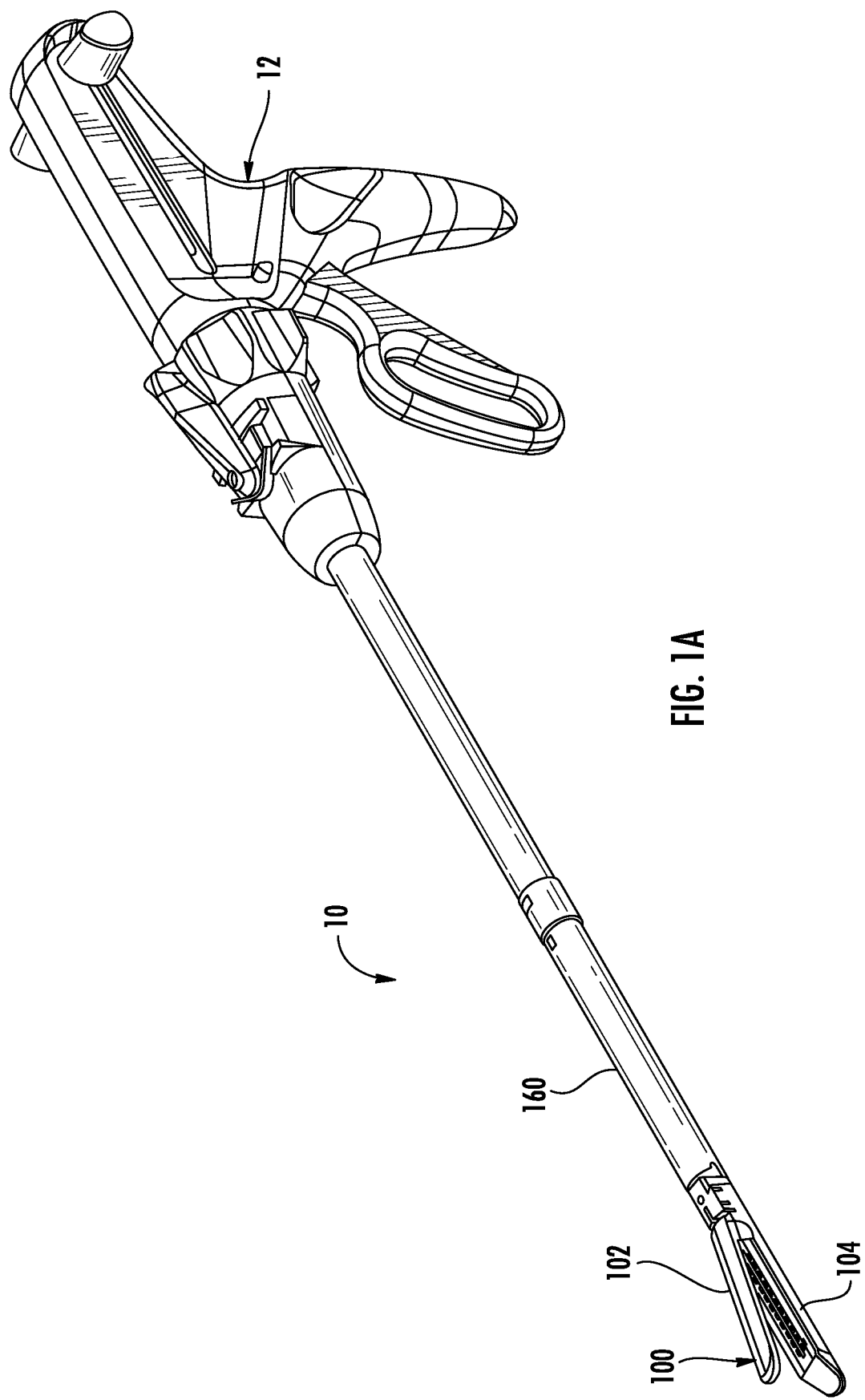
FIG. 1A is a perspective view of an illustrative surgical stapling instrument including a stapling jaw assembly, and an anvil jaw assembly.

FIG. 1A is a perspective view of an illustrative surgical stapling instrument 10 capable of utilizing a locking assembly in accordance with the present disclosure. Surgical stapling instrument 10 includes a handle assembly 12, and an end effector 100 including an anvil jaw assembly 102 and a staple jaw assembly 104 mounted on an elongated shaft 160 of the surgical stapling instrument 10.

Figure 1B:
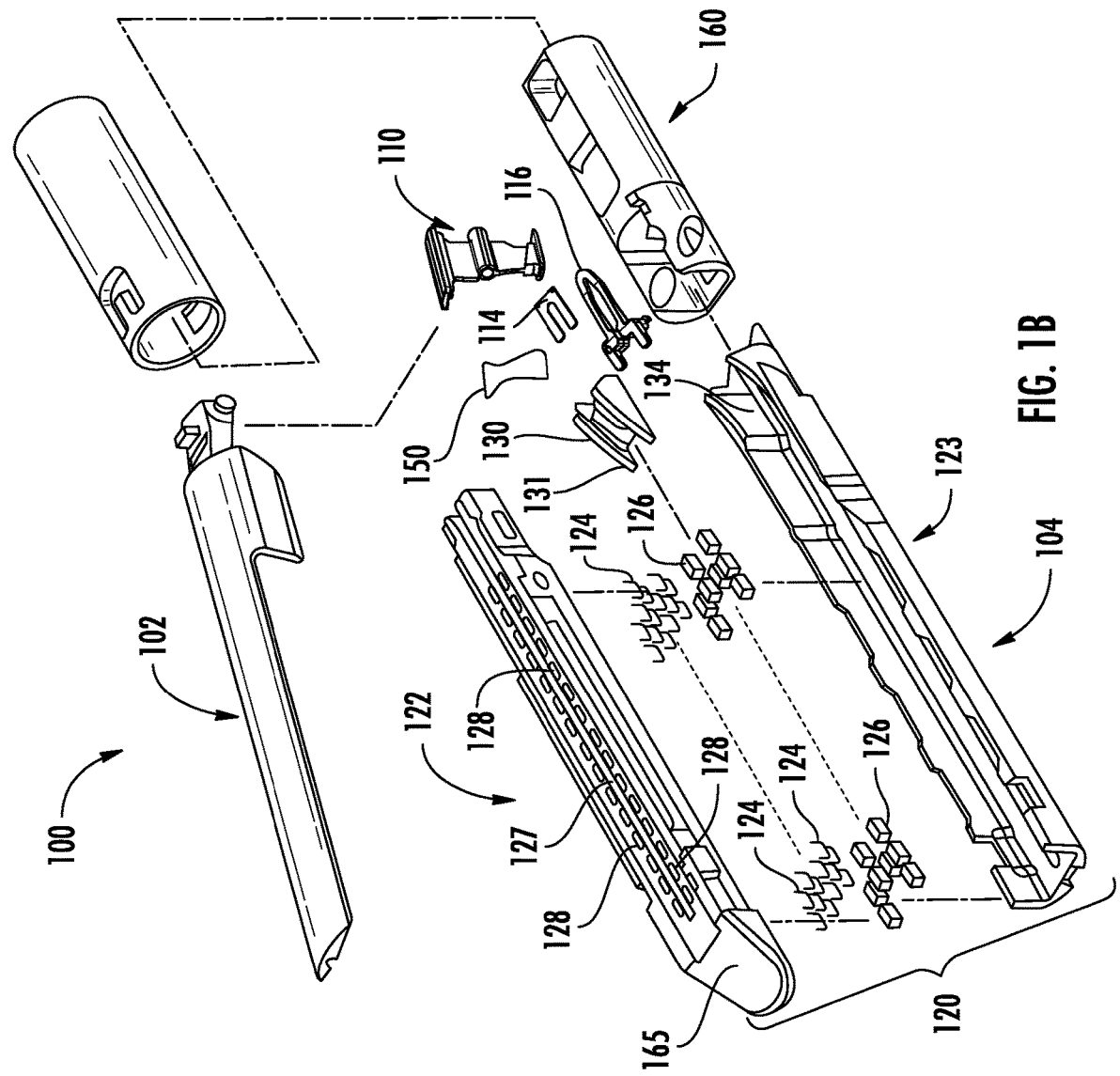
FIG. 1B is an exploded view of an illustrative end effector of a surgical stapling instrument.

FIG. 1B shows anvil jaw assembly 102, including an anvil having staple forming pockets (not shown) supported thereon, and staple jaw assembly 104. Staple jaw assembly 104 and anvil jaw assembly 102 are configured to move from an open position to a closed position. In the open position, a fresh stapling cartridge (sometimes referred to as a reload) can be loaded into staple jaw assembly 104, a spent staple cartridge removed from staple jaw assembly 104, and tissue may be positioned between the jaw assemblies 102, 104. In the closed position, jaw assemblies 102, 104 cooperate to close upon and clamp tissue such that cartridge 122 and the anvil (not shown) are in close cooperative alignment. In the embodiment shown in FIGS. 1A and 1B, staple jaw assembly 104 is stationary and anvil jaw assembly 102 pivots to the open position. In other embodiments it is contemplated that the jaw assembly containing the anvil is stationary and the jaw assembly containing the staple cartridge pivots to the open position. As those skilled in the art reading this disclosure will appreciate, in yet other embodiments both the anvil jaw assembly and the staple jaw assembly may pivot.

With continued reference to FIG. 1B, staple jaw assembly 104 includes a staple cartridge 122 supported in a channel 134 on jaw 123. Cartridge 122 includes a plurality of staples 124 that are supported on corresponding staple drivers 126 provided within respective staple apertures 128 formed in cartridge 122. Cartridge 122 also includes a shuttle 130 having an inclined distal portion 131 that, upon distal movement, sequentially acts on staple drivers 126, camming them upwardly thereby moving staples 124 into deforming contact with the anvil (not shown). Cartridge 122 also includes a knife 150 configured to translate distally through a channel 127 in cartridge 122 and to sever clamped, stapled tissue.

FIG. 1B further shows a drive member 110 movably supported on the surgical stapling instrument such that it may pass distally through cartridge 122 and staple jaw assembly 104 when the surgical stapling instrument is fired (e.g., actuated). Also shown in FIG. 1B is the locking assembly including locking member 116 and spring 114.

With a fresh reload installed, drive member 110 is in a proximal position where it has not yet engaged knife 150 or shuttle 130. Drive member 110 may be any structure capable of pushing at least one of a shuttle or a knife of a surgical stapling instrument with the necessary force to effectively sever or staple human tissue. Drive member 110 may be an I-beam, an E-beam, or any other type of drive member capable of performing similar functions.

For a more detailed description of illustrative end effectors, reference may be made to U.S. Pat. Nos. 6,669,073 and 8,800,841, the entire contents of which are incorporated herein by this reference. It should of course, be understood that end effector shown in FIGS. 1A and 1B is merely illustrative, and that other end effectors may be employed, including but not limited to the end effectors shown in WO2014/106275, the entire contents of which are incorporated herein by this reference.

Figure 2A:
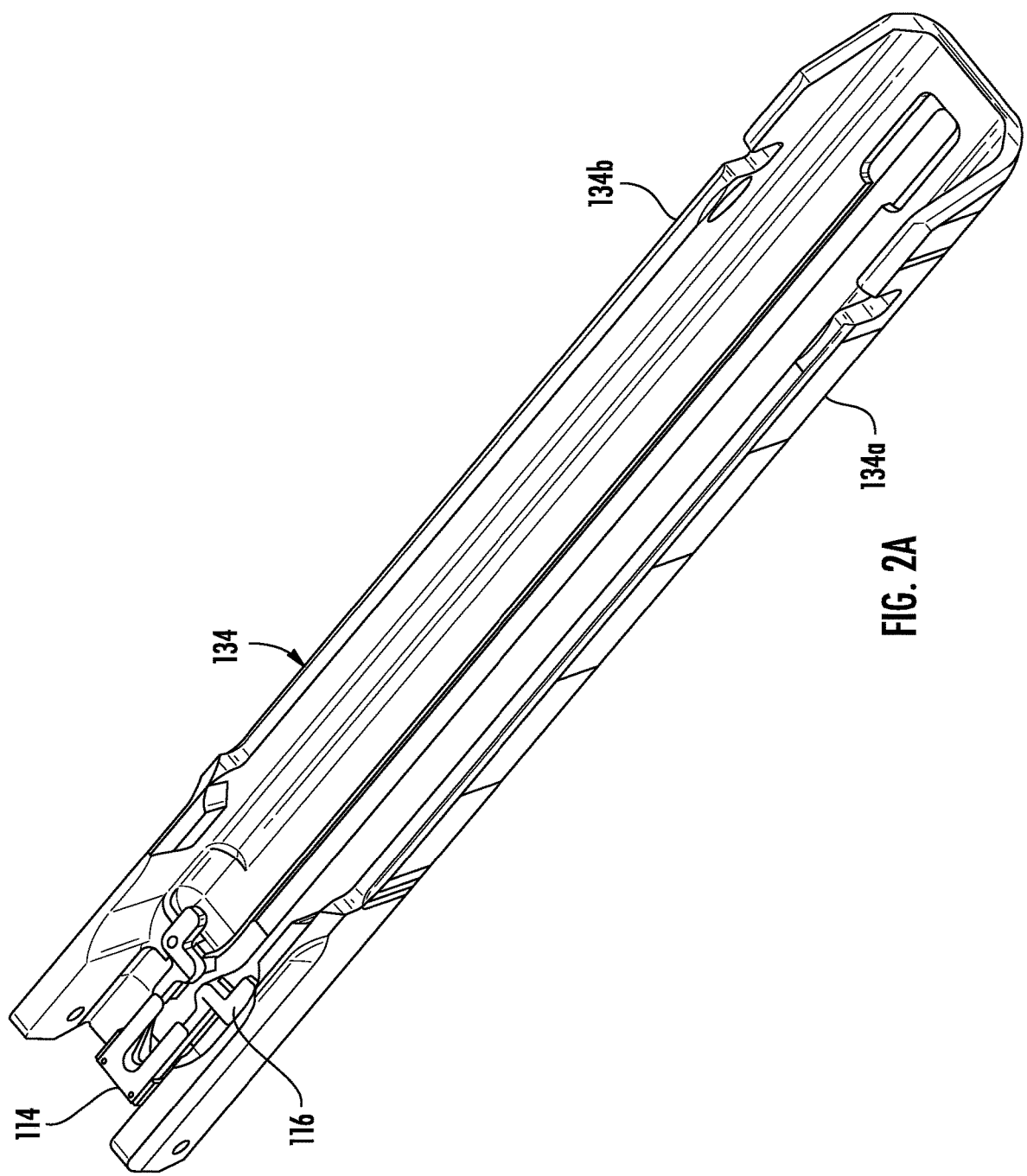
FIG. 2A is a top perspective view of the channel and locking assembly of the end effector of FIG. 1B.

FIGS. 2A and 2B show channel 134, spring 114, and locking member 116 of the end effector of a surgical stapling instrument in accordance with an embodiment of the present disclosure. Channel 134 includes two side walls 134a, b and a bottom wall 134c.

In an illustrative embodiment of a surgical stapling instrument in accordance with this disclosure, locking member 116 is positioned in the proximal end of channel 134. Spring 114 serves to bias locking member 116 into a second position preventing distal movement of a drive member 110 (See FIG. 7).

Figure 4:
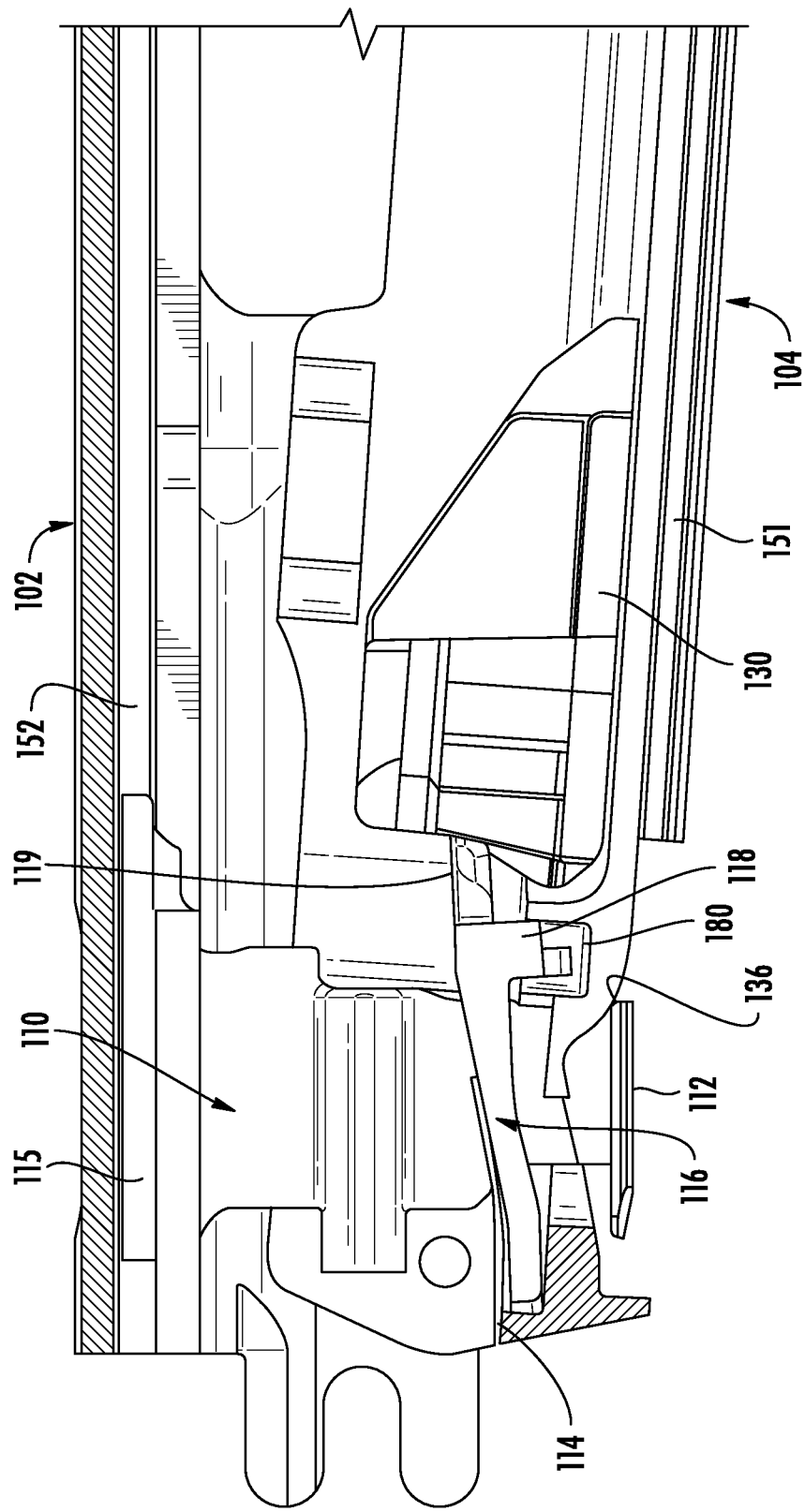
FIG. 4 is a partial cross-sectional side view of the end effector of the end effector of FIG. 1B in a partially closed position.
Figure 5:
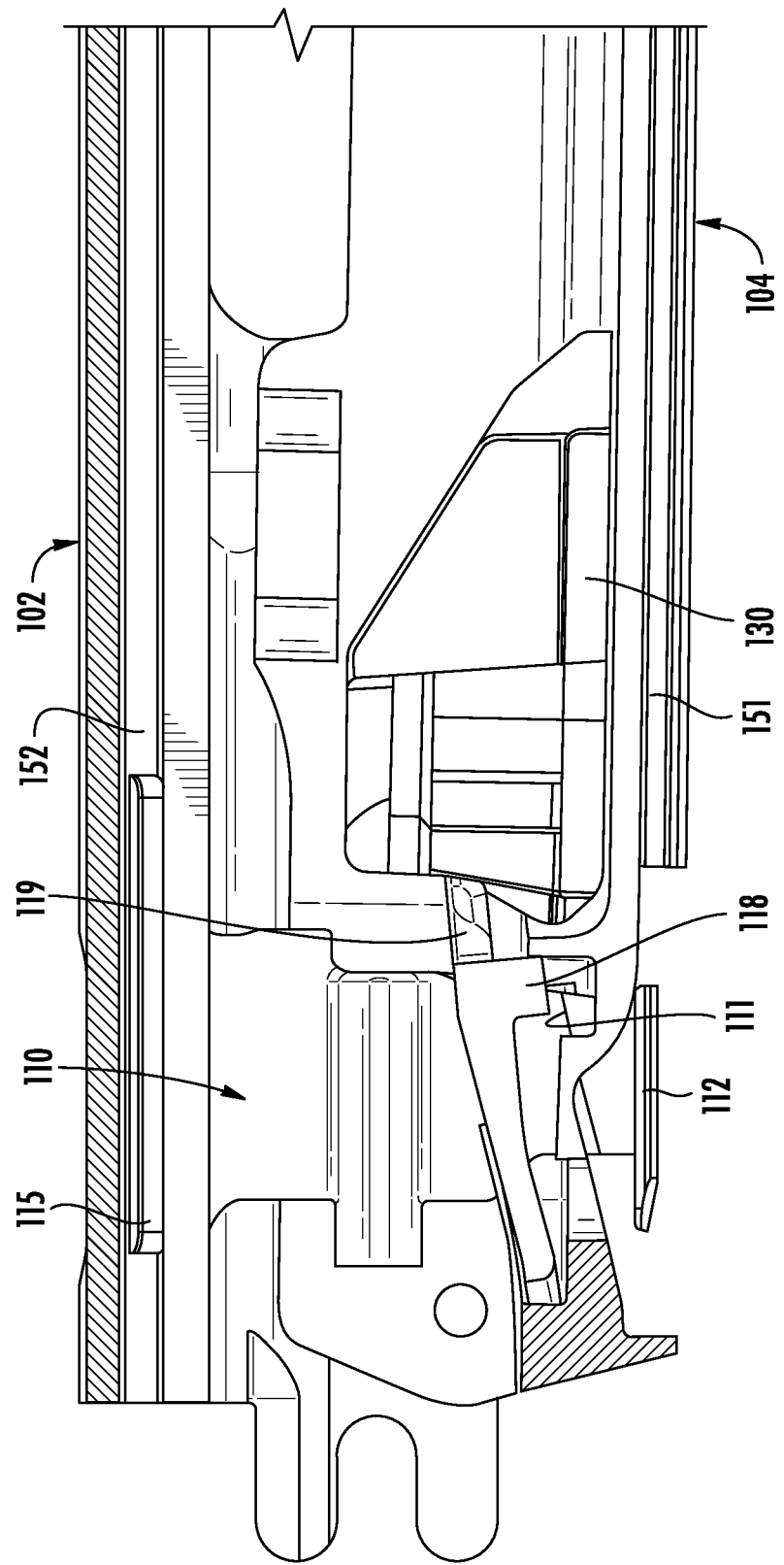
FIG. 5 is a partial side, cross-sectional view of the end effector of the end effector of FIG. 1B in a substantially closed position.

FIGS. 3-5 illustrate the interaction of drive member 110 with a cam surface 136 of the channel 134 to simultaneously pivot channel 134 and its contents.

As seen in FIG. 3, an illustrative surgical stapling instrument may include drive member 110 having a footer 112, spring 114, channel 134 having a cam surface 136, and locking member 116. Also shown in FIG. 3 is shuttle 130, which is contained within staple cartridge 122, the structure of which is not shown in this view.

As a user manipulates handle assembly 12 to close the jaws of the surgical stapling instrument, drive member 110 moves distally, causing a footer 112 of the drive member to come into contact with cam surface 136 of channel 134. As shown in FIGS. 4-6, as drive member 110 rides along cam surface 136, simultaneous pivoting of the channel 134, the shuttle 130, and the locking member 116 towards the anvil jaw assembly is achieved.

The timing of this pivoting allows for a ramped portion 111 of the drive member to clear underneath an engagement portion 118 of locking member 116, as shown in FIG. 5. During pivoting, distal portion 119 of locking member 116 is resting on shelf 132 of shuttle 130, (See FIG. 6A) and is therefore in a first position allowing for distal translation of drive member 110. In this first position, engagement portion 118 of the locking member 116 is positioned above a slot 180 in channel 134.

FIGS. 6-9 sequentially illustrate the actuation of an illustrative surgical stapling instrument in accordance with the present disclosure.

Figure 6A:
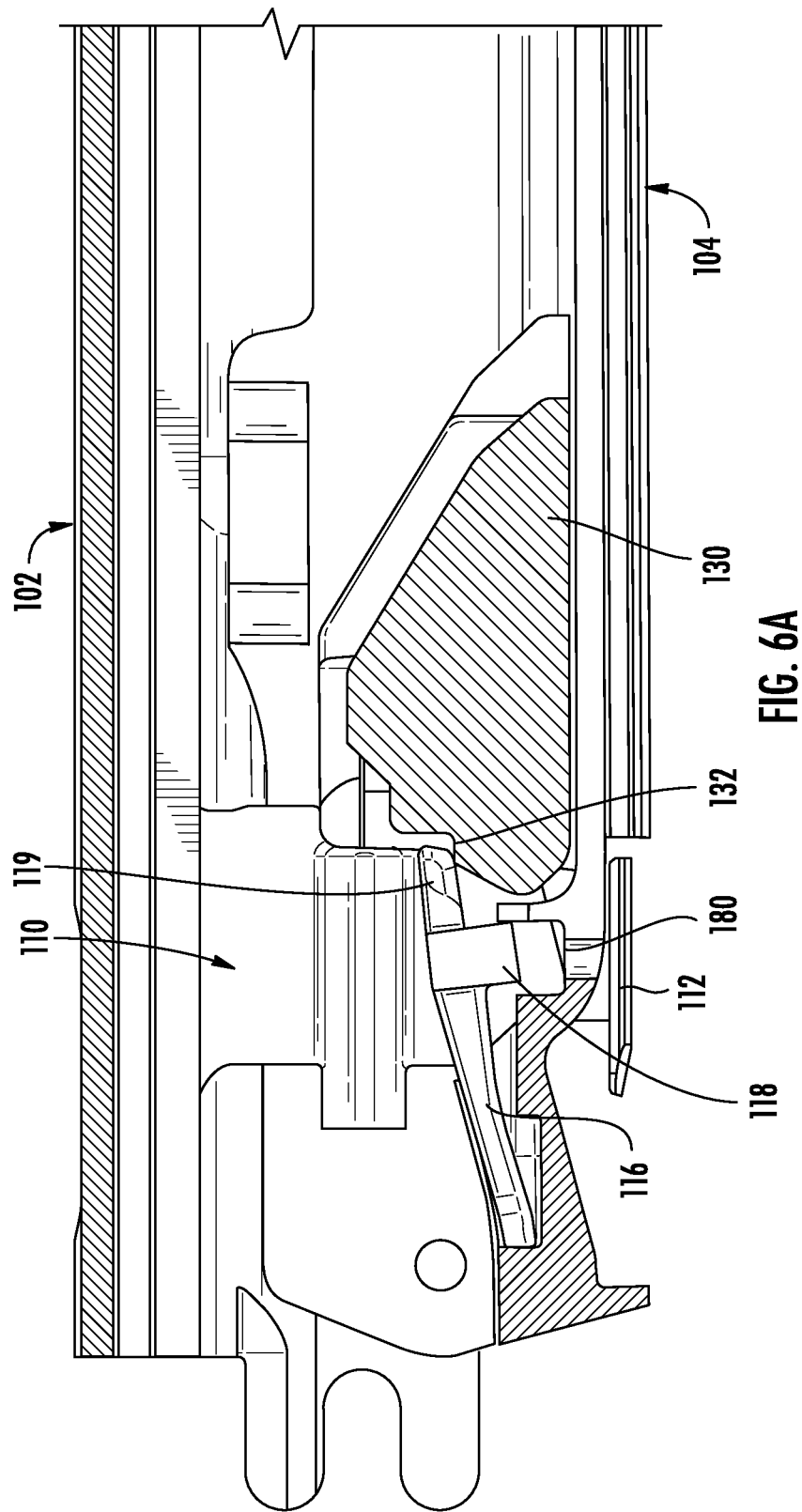
FIG. 6A is a side cross-sectional view of the end effector of FIG. 1B in a closed position.
Figure 6B:
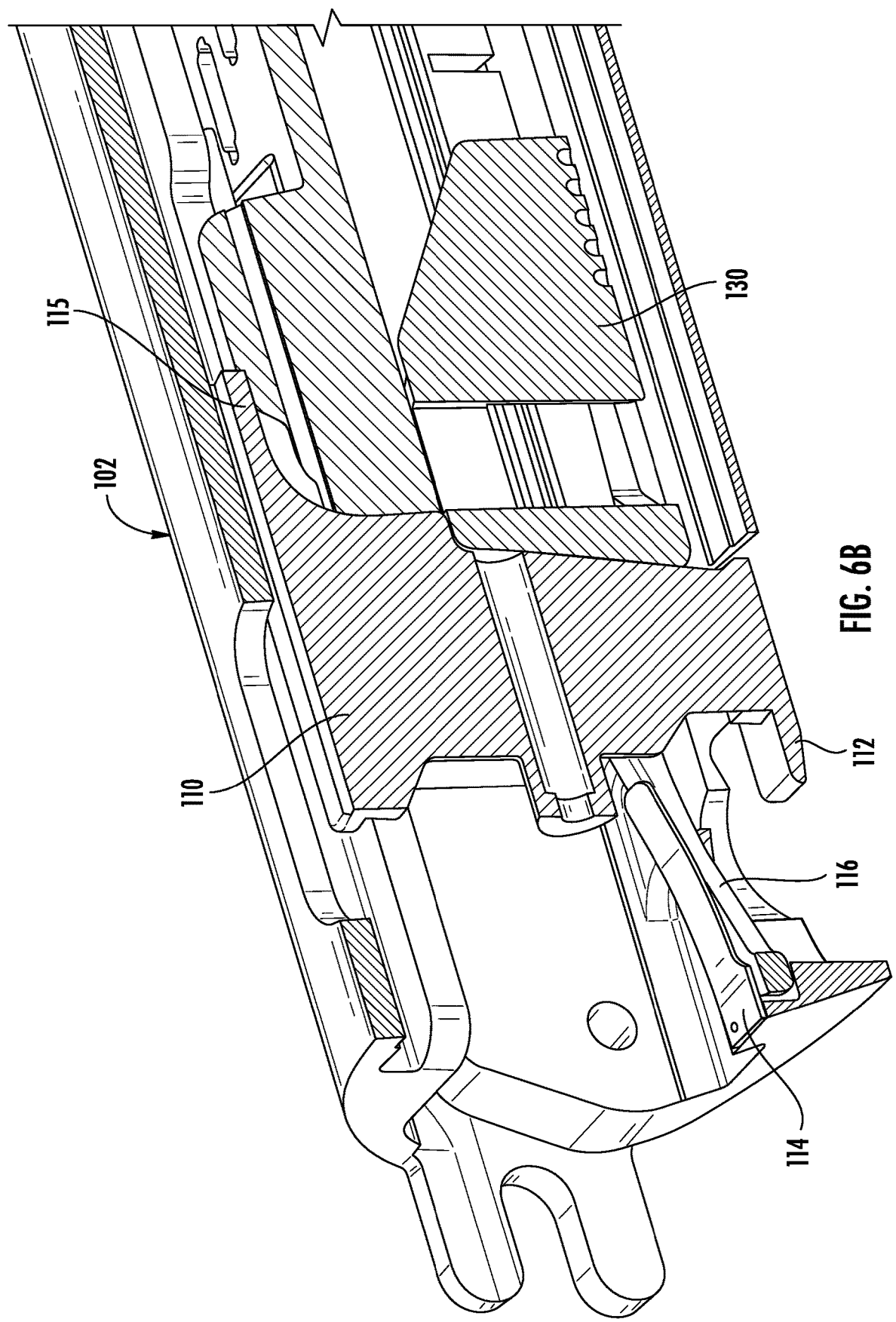
FIG. 6B is a partial rear perspective view of the end effector in the closed position with a staple cartridge in place.

In FIGS. 6A and B, the actuation stroke has begun and drive member 110 has advanced distally to contact shuttle 130, but shuttle 130 has not yet moved. Lower ramped portion 111 is still able to pass underneath locking member 116, as the locking member continues to rest on the shelf 132 of shuttle 130 and is in the first unlocked position.

Figure 7:
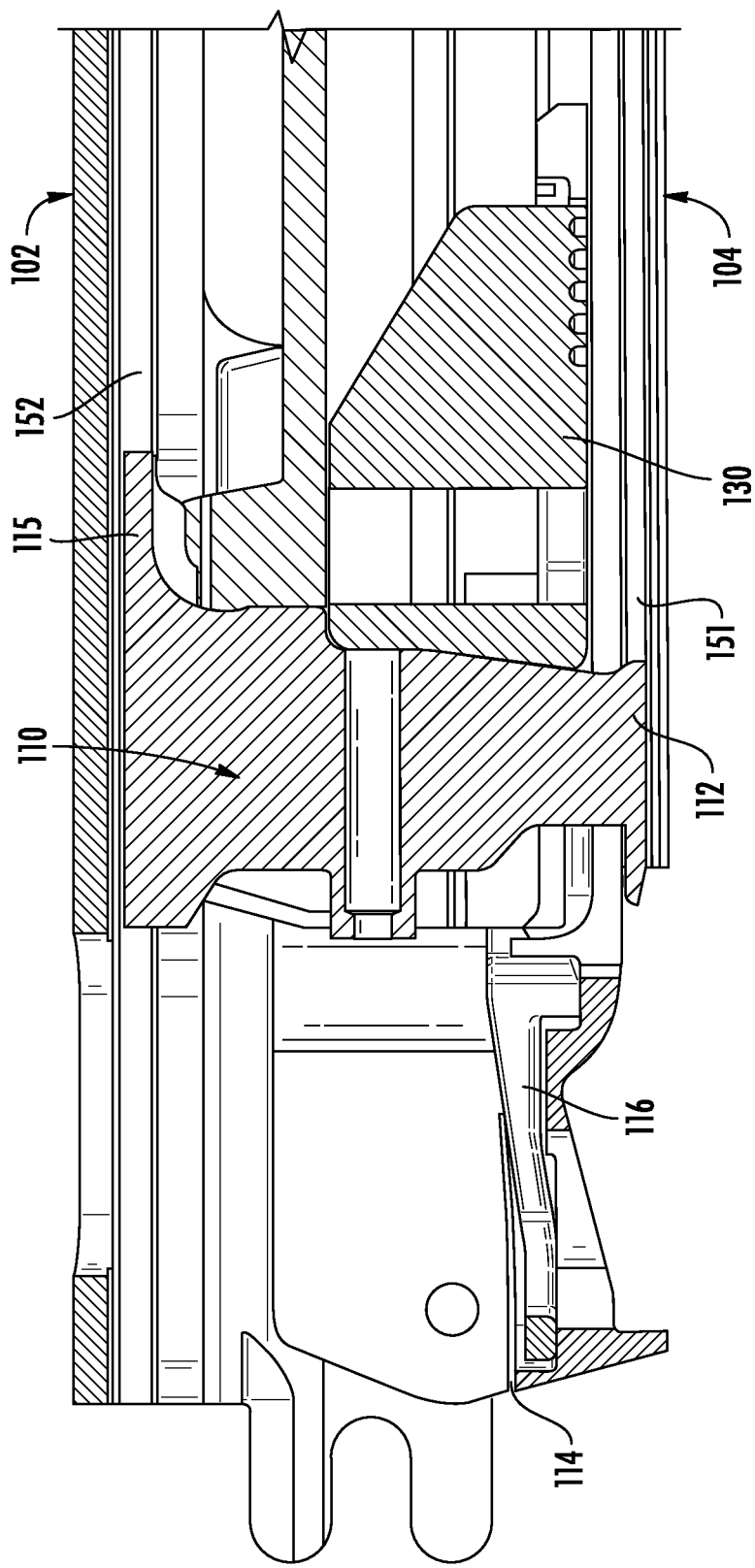
FIG. 7 is a partial side, cross-sectional view of the end effector of FIG. 1B showing the locking member in the locking position.

In FIG. 7, drive member 110 continues to travel distally down channel 134, translating shuttle 130 in a distal direction. Once shuttle 130 starts to translate distally, locking member 116 falls off of shelf 132 of shuttle 130 causing engagement portion 118 of locking member 116 to move to a second locking position by falling into and engaging slot 180, thereby enabling the locking mechanism. Spring 114 is configured to bias engagement portion 118 of locking member 116 toward slot 180 to keep the locking mechanism enabled.

Figure 8:
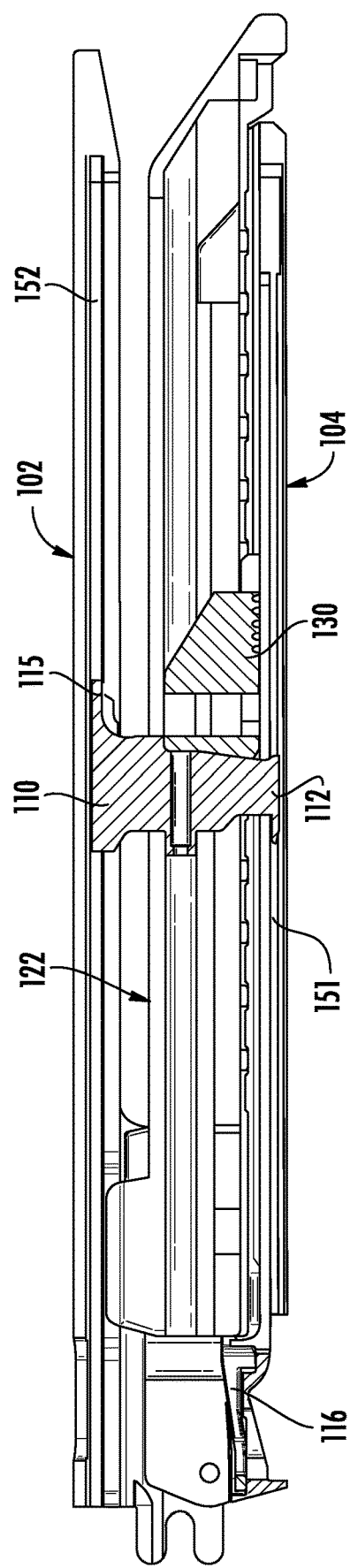
FIG. 8 is a partial side, cross-sectional view of the end effector of FIG. 1B showing the drive member and shuttle advanced distally.

As drive member 110 continues to move distally, as shown in FIG. 8, footer 112 rides within slot 151 formed in the bottom wall 134c of channel 134 and top member 115 of drive member 110 rides within slot 152 of anvil assembly 102 to maintain the jaw assemblies 102, 104 spaced a constant distance from each other.

Ultimately, as shown in FIG. 9, drive member 110 translates distally through a complete firing stroke during which stapling and severing of tissue have occurred. Drive member 110 can then be retracted, leaving shuttle 130 parked at a position in a distal portion of cartridge 122. In embodiments, such as the embodiment illustrated in FIG. 9 shuttle 130 may be unable to move proximally towards the home position due to friction with cartridge 122. In embodiments, a knife may be integrally formed with drive member 110. In embodiments, a separate knife 150 (See FIG. 1B) may be translated distally by drive member 110 and may be parked in a predetermined position in a distally located garage 165, the garage 165 including lateral surfaces that face the cutting edge of knife 150.

Figure 10B:
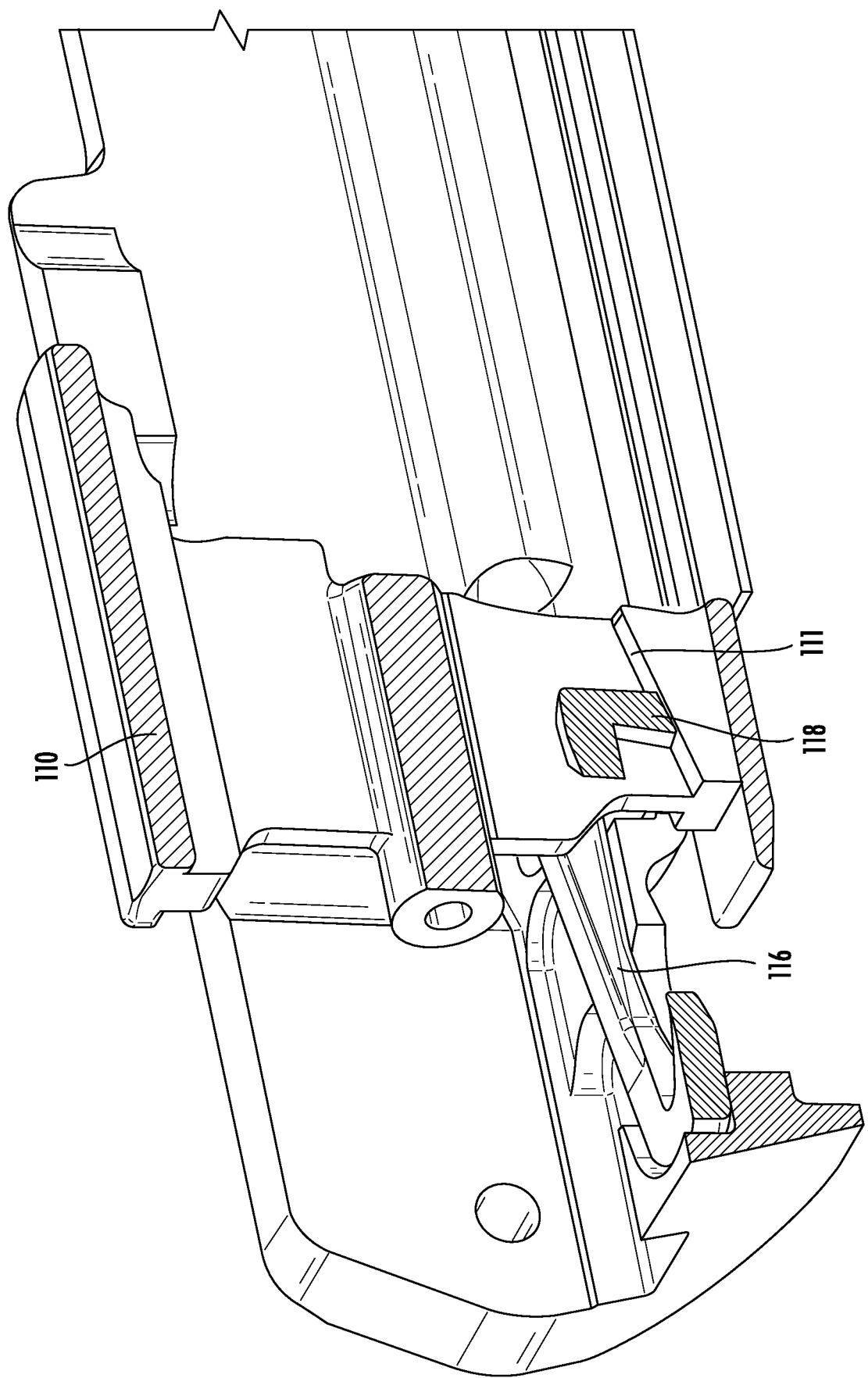
FIG. 10B is a partial perspective view of FIG. 10A.
Figure 11:
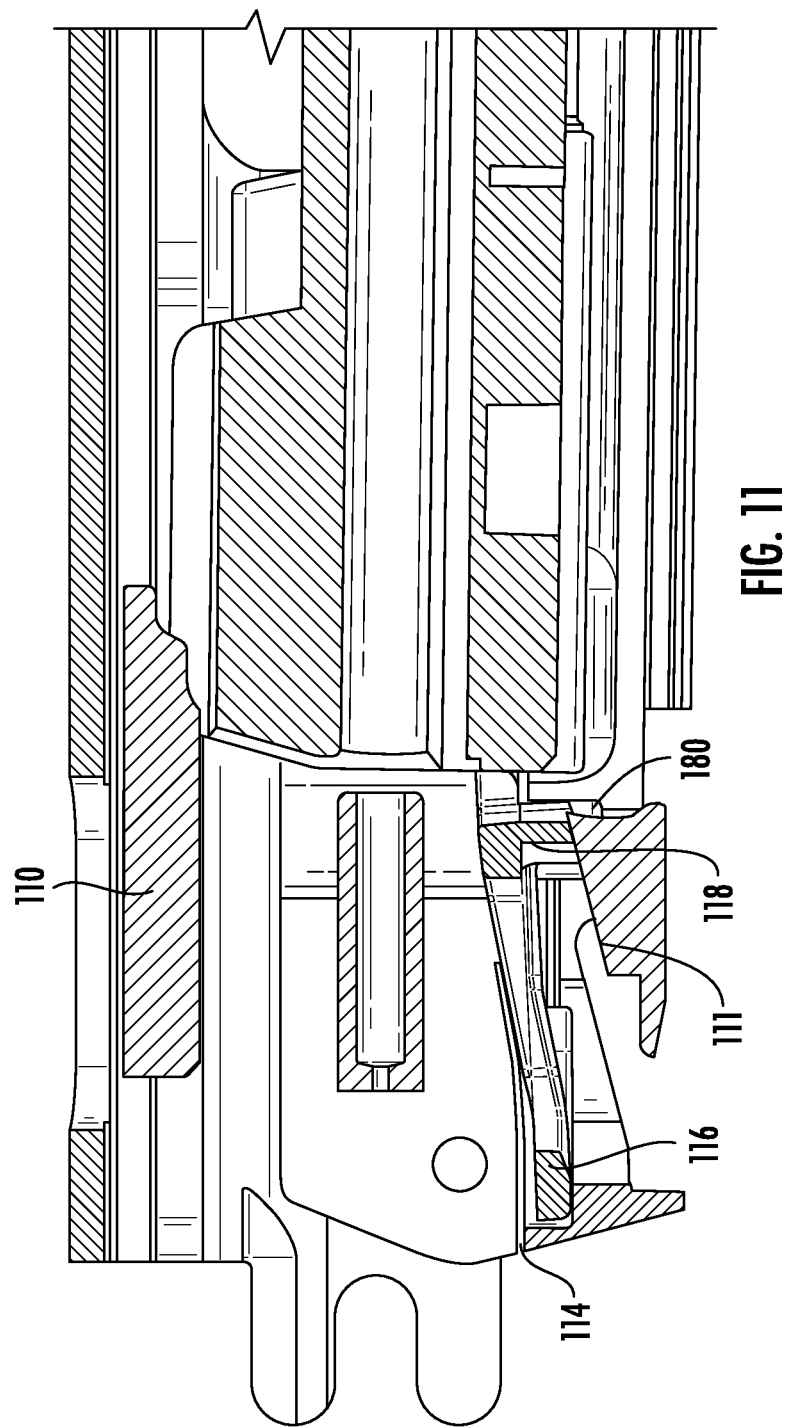
FIG. 11 is a partial cross-sectional view of the end effector of FIG. 1B illustrating a ramped portion of the drive member riding under the locking member during retraction.

FIGS. 10A and B and 11 illustrate retraction of drive member 110 after a firing stroke has been completed. As drive member 110 is retracted to the proximal end of the end effector, lower ramped portion 111 of drive member 110 contacts and rides under engagement portion 118 of locking member 116, causing locking member 116 to be pushed upwards against the bias of spring 114. Once locking member 116 has passed over the entirety of lower ramped portion 111 of drive member 110 as seen in FIG. 12, the bias of spring 114 again forces engagement portion 118 of locking member 116 to fall back into and engage slot 180, thereby engaging the locking mechanism.

Figure 12:
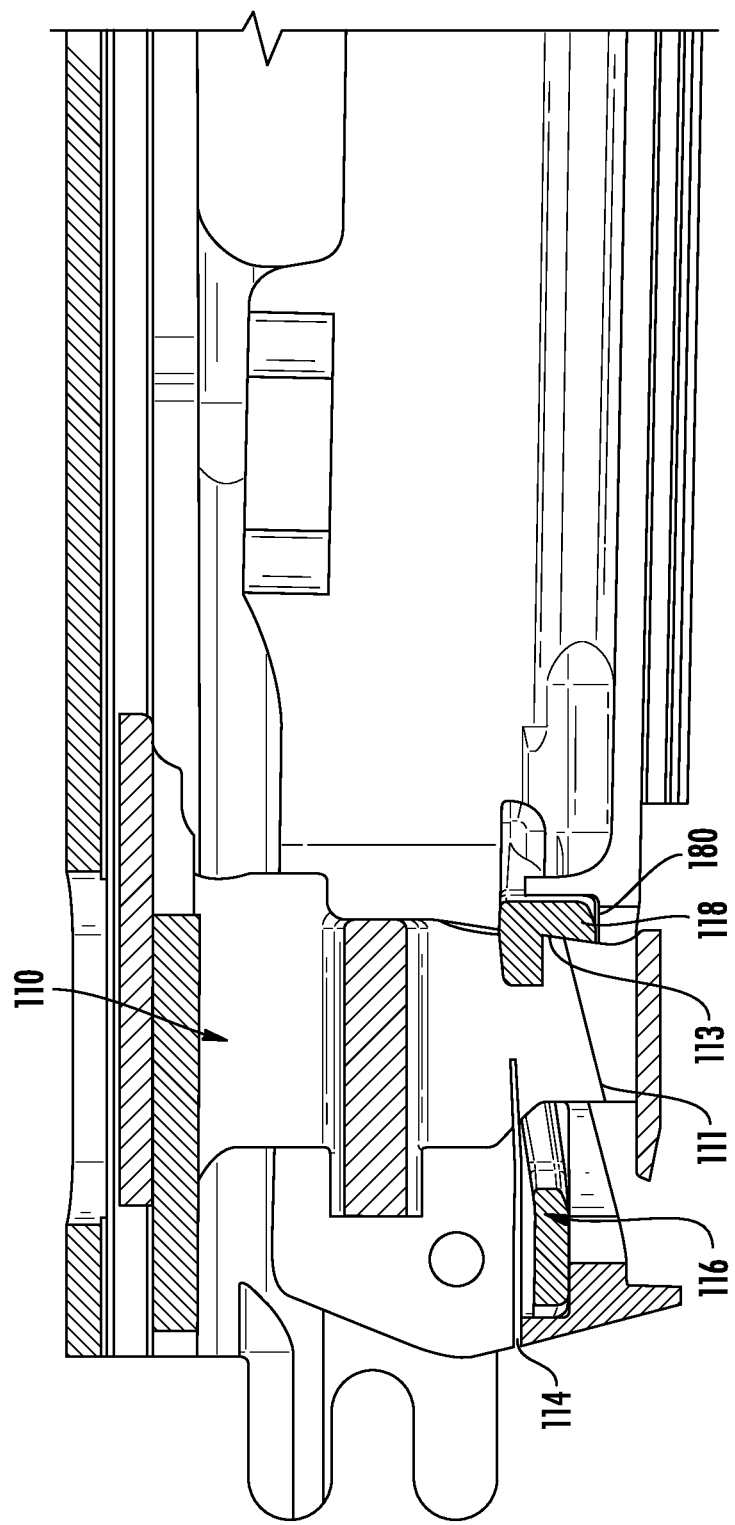
FIG. 12 is a partial cross-sectional view of the end effector of FIG. 1B illustrating the drive member retracted sufficiently to allow the locking member to move to the locking position.
Figure 13:
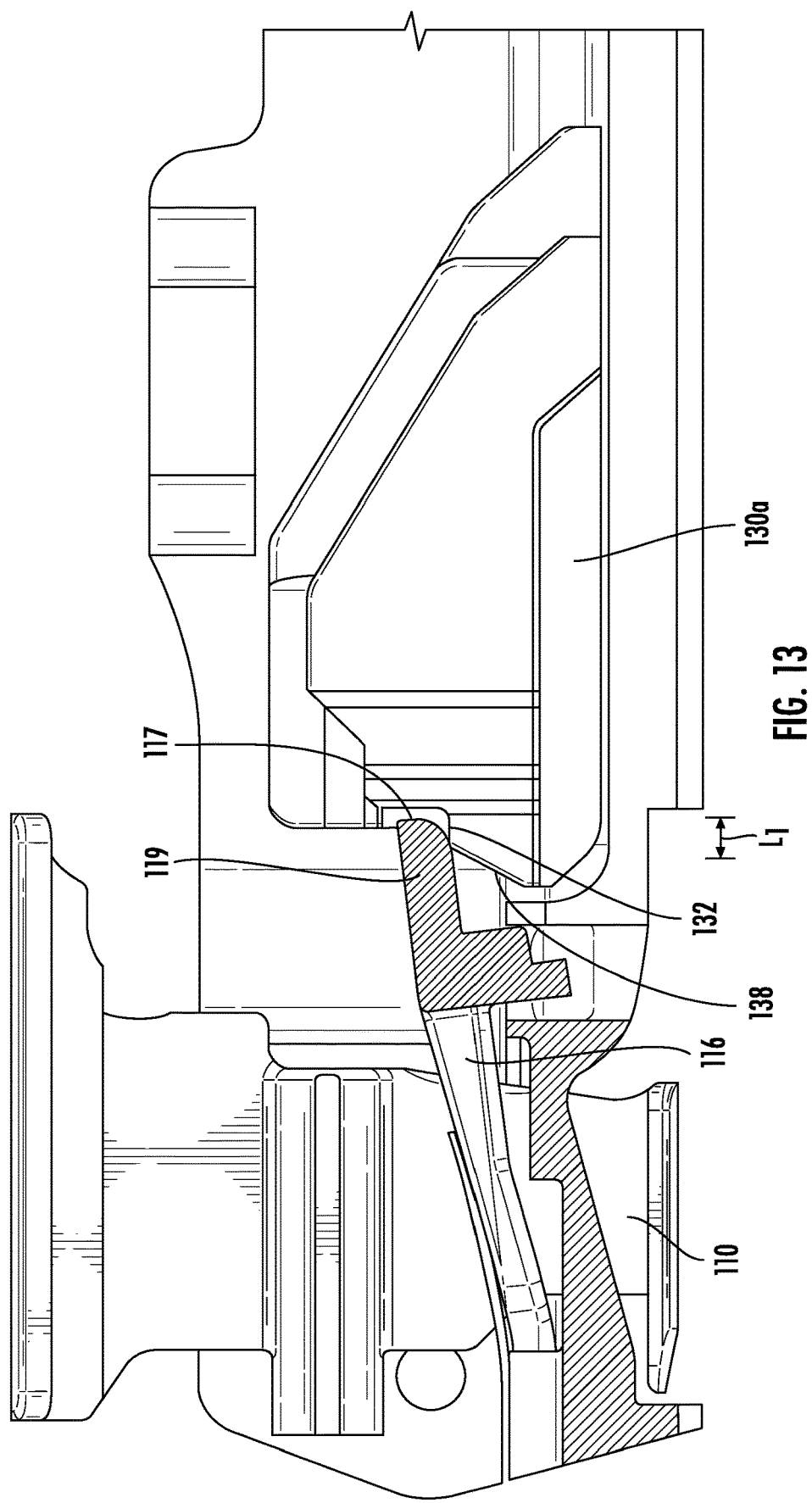
FIG. 13 is a partial cross-sectional view of the end effector of FIG. 1B illustrating a reload-specific shuttle engaging a distal portion of a locking member.
Figure 14:
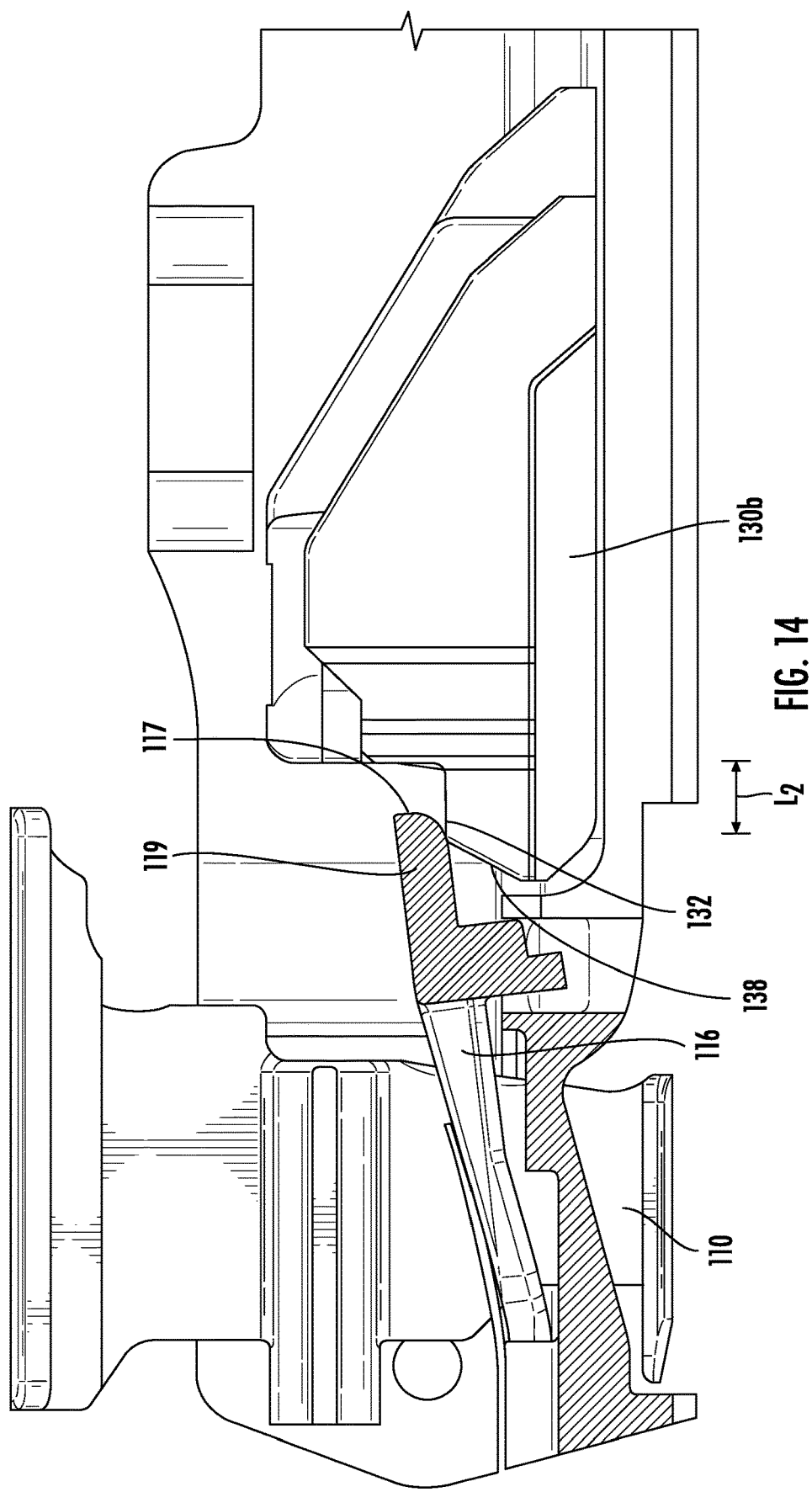
FIG. 14 is a partial cross-sectional view of the end effector of FIG. 1B illustrating another embodiment of a reload-specific shuttle engaging a distal portion of the locking member.
Figure 15:
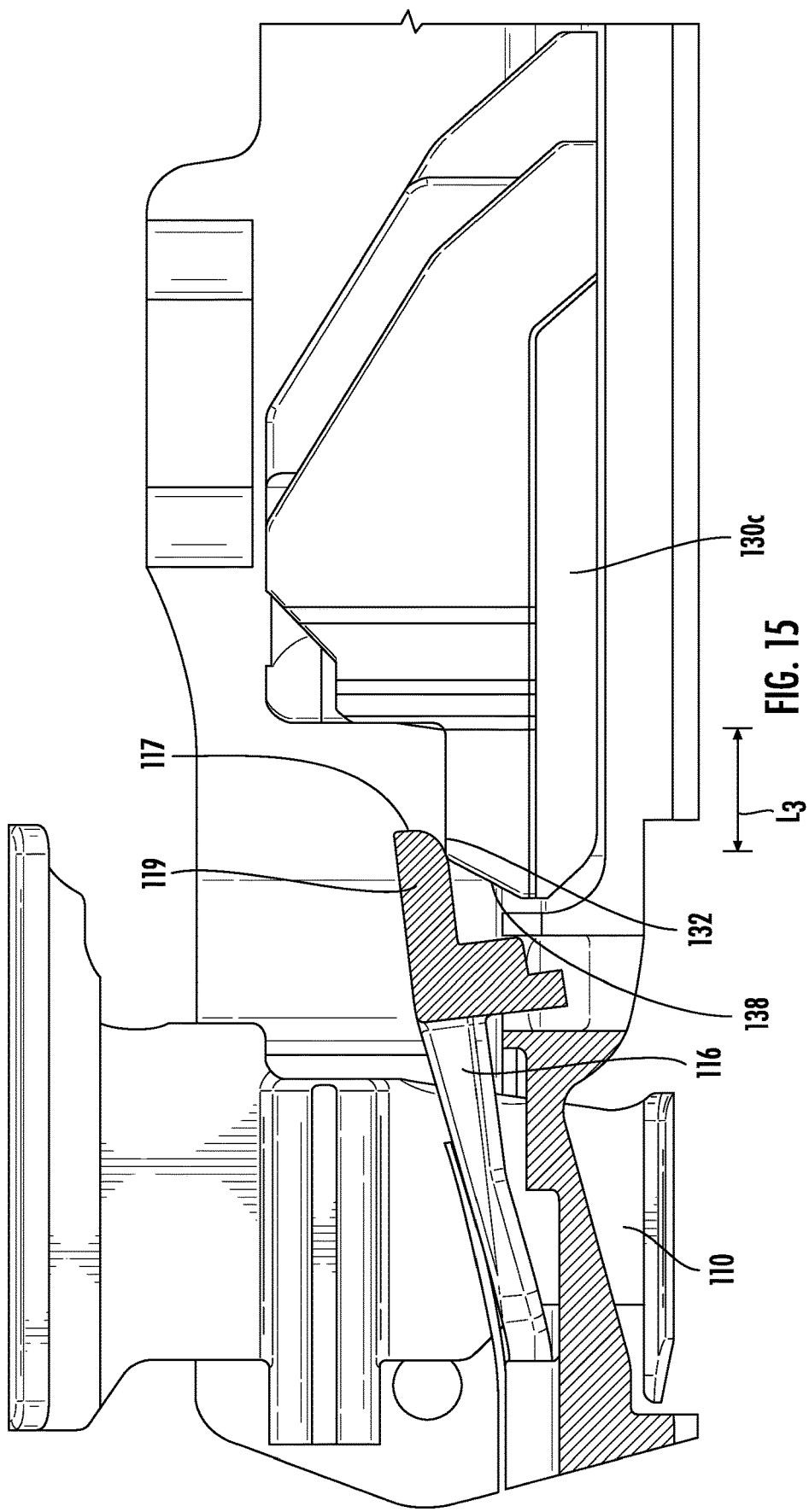
FIG. 15 is a partial cross-sectional view of the end effector of FIG. 1B illustrating a third embodiment of a reload-specific shuttle engaging a distal portion of the locking member.
Figure 16:
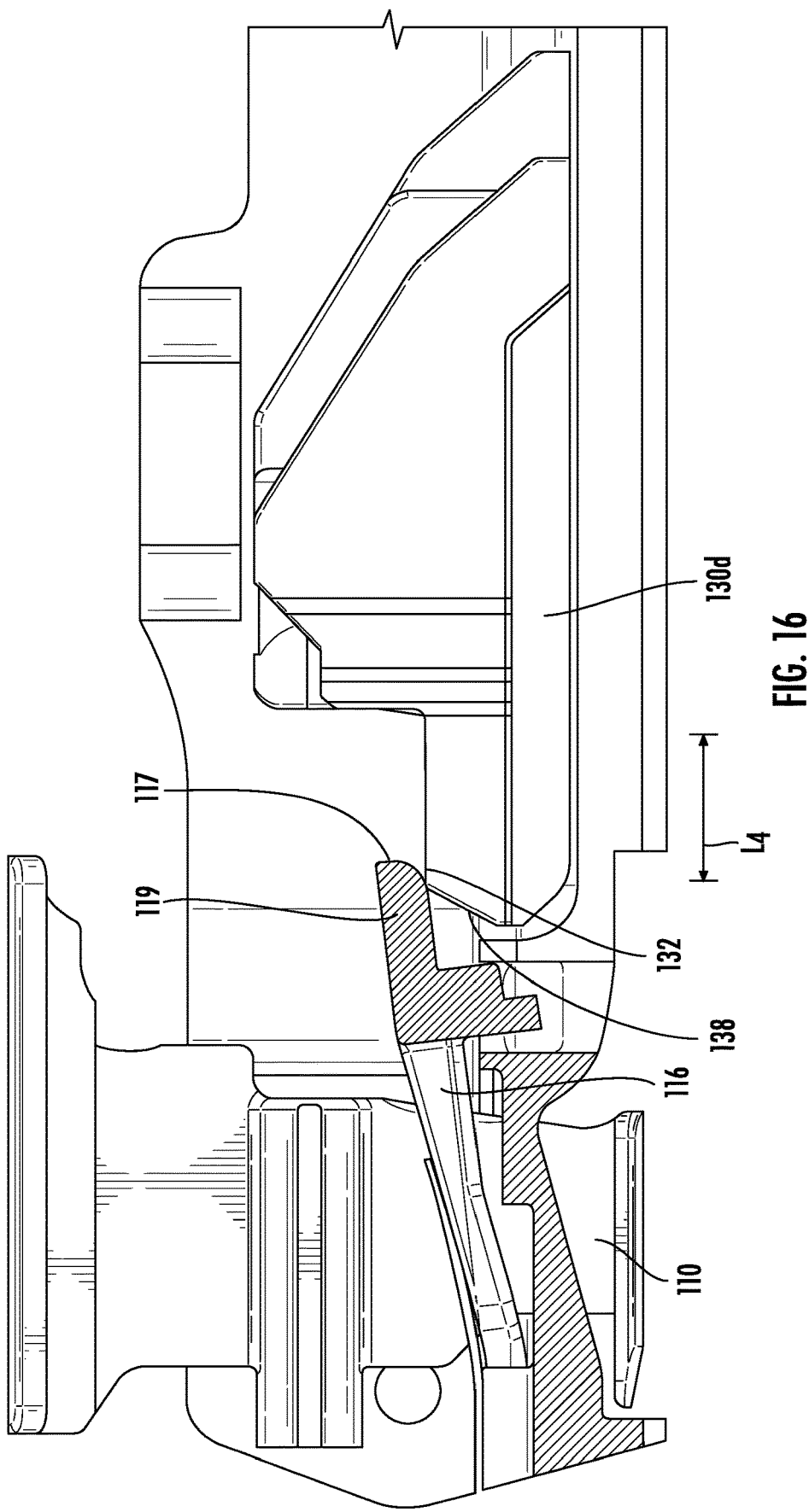
FIG. 16 is a partial cross-sectional view of the end effector of FIG. 1B illustrating a fourth embodiment of a reload-specific shuttle engaging a distal portion of the locking member.

FIG. 12 shows an illustrative embodiment of a surgical stapling instrument that has been locked out. If a user attempts to actuate a surgical stapling instrument in this position, a distal face 113, located on the distal end of lower ramped portion 111 of drive member 110, will abut the proximal side of engagement portion 118 of locking member 116, preventing distal translation of drive member 110, thereby preventing actuation of the surgical stapling instrument.

Because the staple cartridge is spent and there is no proximally-positioned shuttle to support locking member 116 out of engagement with slot 180, any attempt to re-fire the surgical stapling instrument will be prevented by drive member 110 engaging locking member 116. The only way to again actuate the surgical stapling instrument is to install a fresh, unfired reload.

Surgical stapling instruments in accordance with embodiments of this disclosure may be configured to accept and utilize a number of different types of reloads where the different types of reloads have various sizes and arrangements of staples. In embodiments, different reloads may contain reload-specific shuttles 130a-130d having shelves 132 of various lengths ($L_1$-$L_4$) to accommodate the variations in staple configurations. As shown in FIGS. 13-16, these different reloads, despite having different length shelves on the shuttle, all contact the locking member at the same position and angle to urge the locking member onto the shelf. In embodiments, these reloads may be color-coded to indicate the staple configuration and may be utilized in conjunction with a robotics system capable of detecting the type of reload based upon the length of the shelf of the shuttle contained in a given reload.

When each type of reload or cartridge 122 is installed, a proximal ramped edge 138 of shuttle 130 engages a ramped surface 117 on distal portion 119 of locking member 116. The proximal movement of cartridge 122 during installation causes proximal ramped edge 138 of shuttle 130 to slide along ramped surface 117 of distal portion 119 of locking member 116 so that distal portion 119 moves up and onto shelf 132 of shuttle 130, thereby placing the locking member 116 in the first, unlocked position allowing the re-loaded surgical stapling instrument to be actuated and drive member 110 to translate distally through a staple firing stroke as described above.

Figure 17:
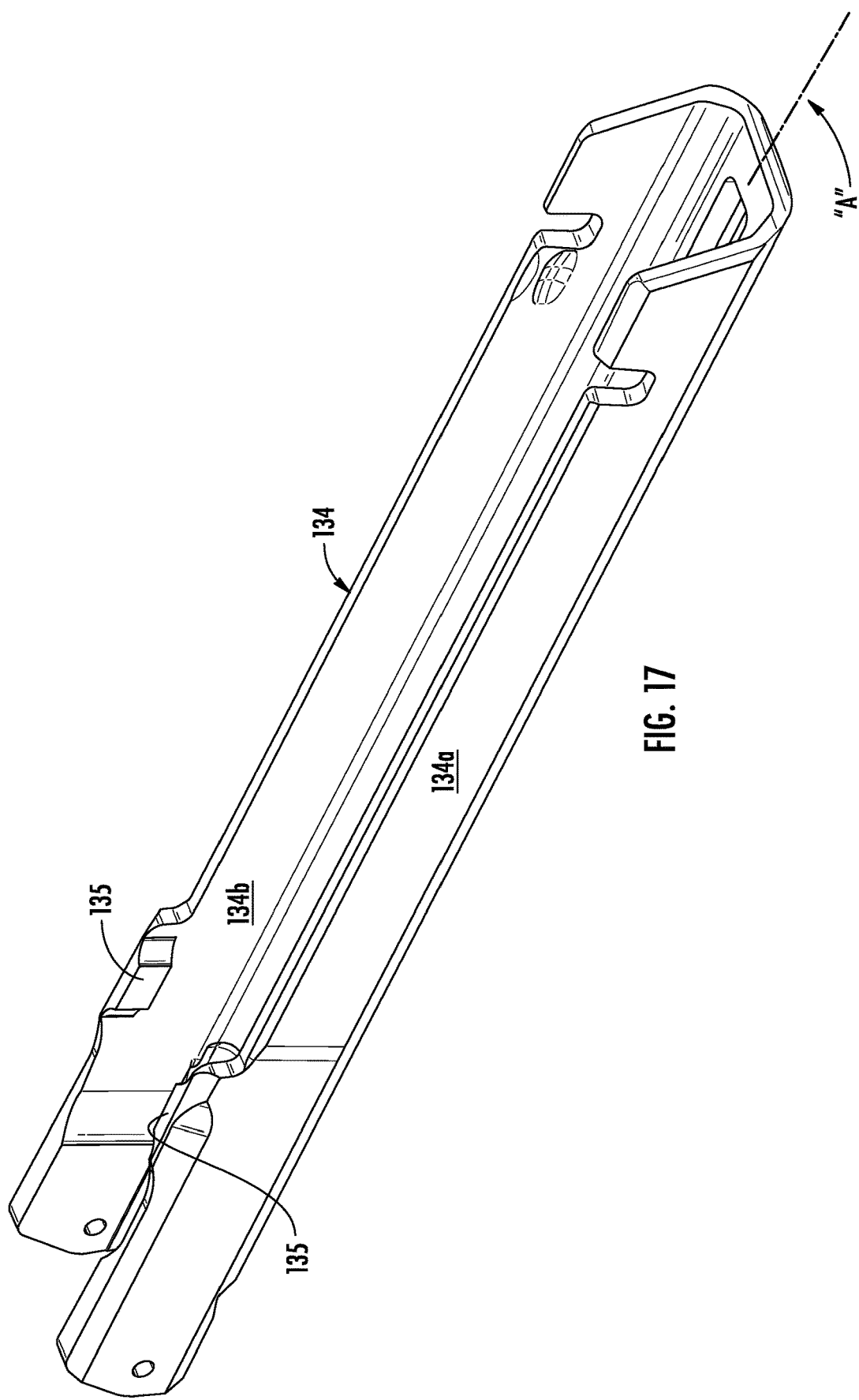
FIG. 17 is a perspective view of the channel of an embodiment of a staple jaw assembly having a guide structure present on the sidewalls of the channel.
Figure 18:
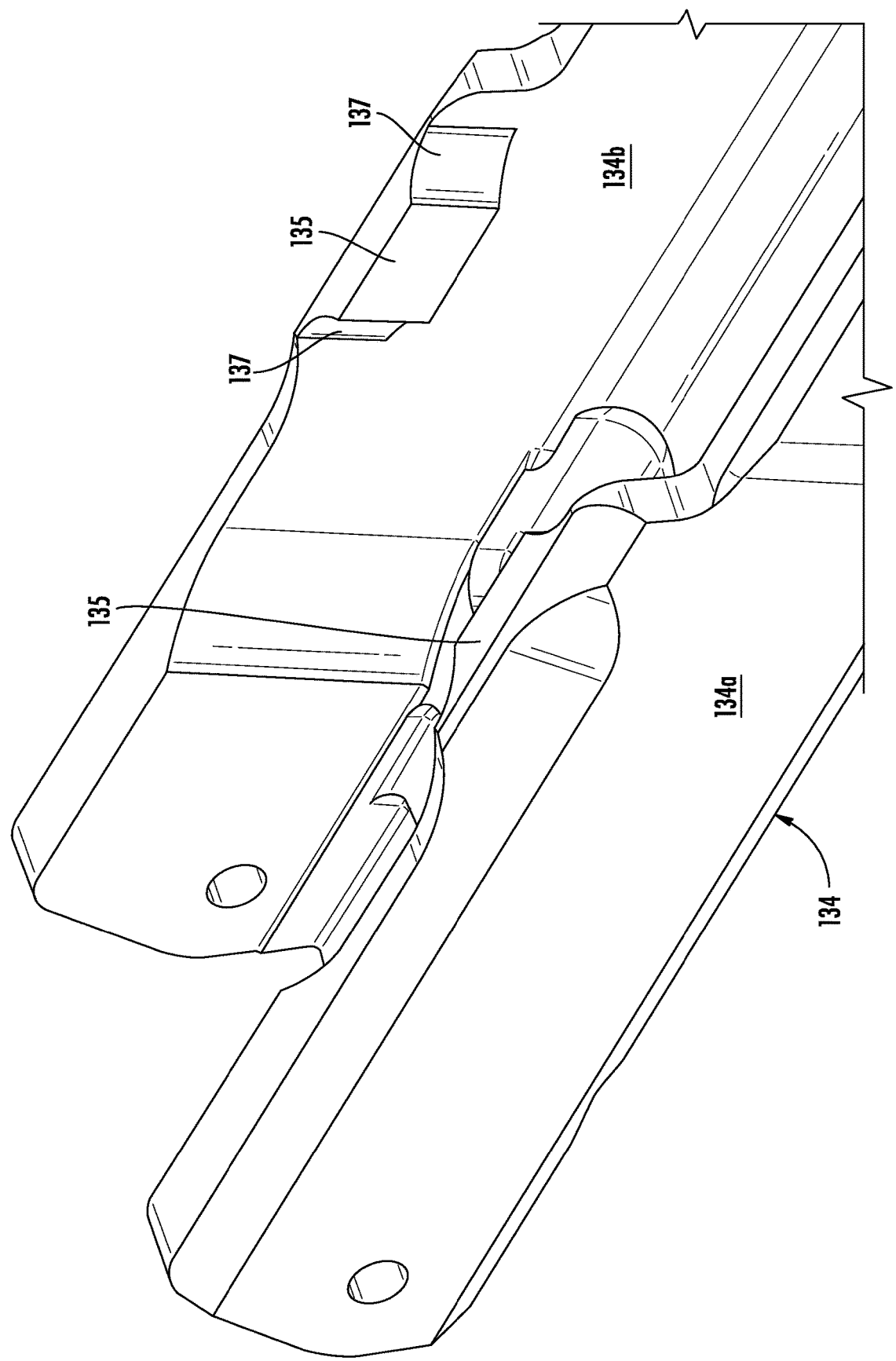
FIG. 18 is a close-up of the guide structure of FIG. 17.

FIG. 17 illustrates a feature for ensuring proper alignment when installing an unfired cartridge (also referred to as a fresh reload). In embodiments, guide structures 135 are formed on sidewalls 134a,b of channel 134 at a substantially proximal position on channel 134. As best seen in FIG. 18, guide structures 135 may contain ramped portions 137 extending in both the proximal and distal directions.

Figure 19:
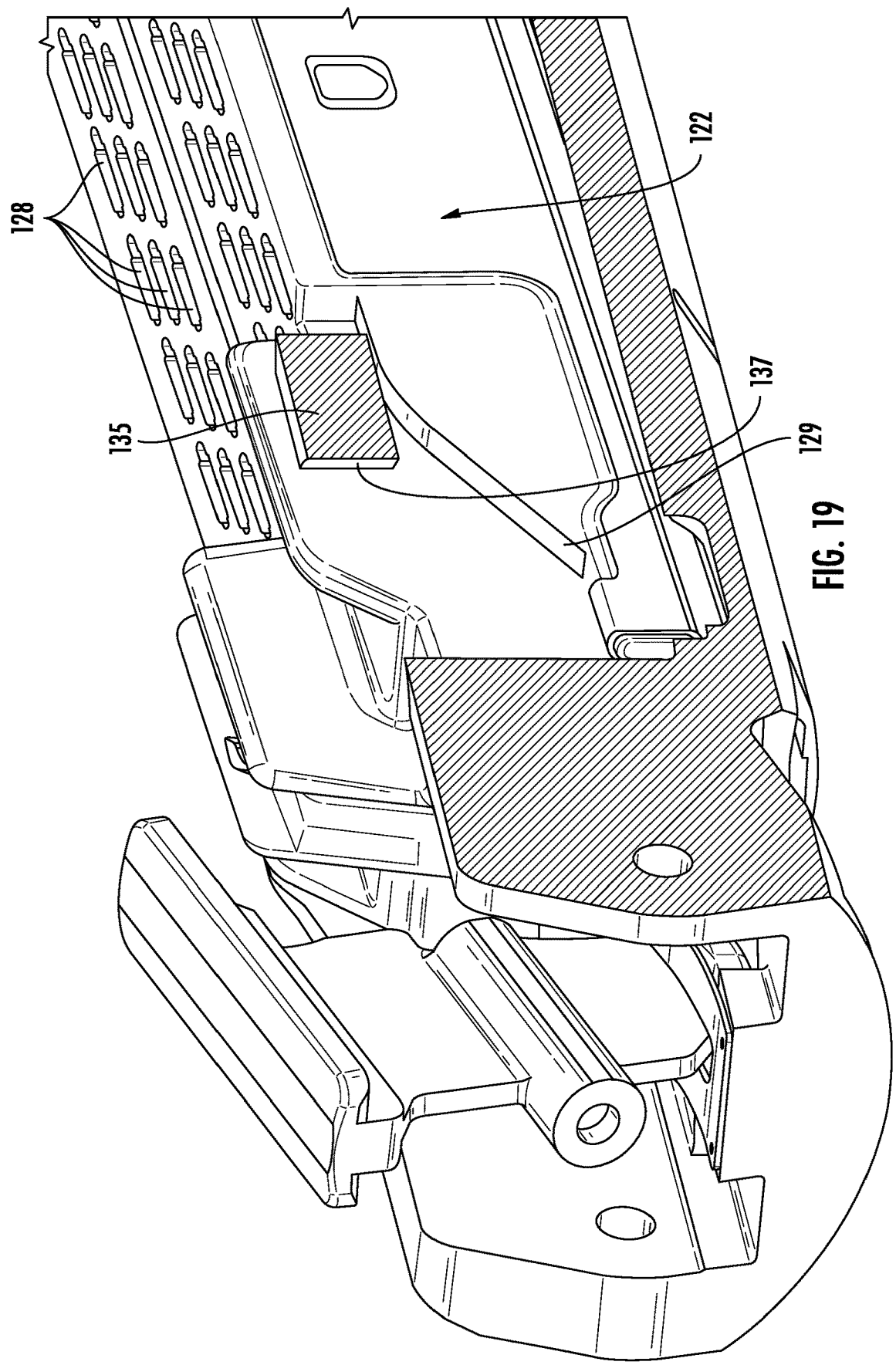
FIG. 19 is a partial perspective view of a reload being installed into the channel of a surgical stapling instrument in accordance with the embodiment of FIG. 18, with one of the sidewalls of the channel removed.

FIG. 19 illustrates an unfired, fresh reload being installed into an illustrative embodiment of a surgical stapling instrument in accordance with this disclosure. Upon installation of the reload, a ramp 129 on cartridge 122 slides underneath guide structure 135, facilitating proper alignment upon reloading. It may be appreciated by those of skill in the art that ramped portions 137 of guide structure 135 help to prevent any edges or corners of cartridge 122 from unintentionally catching on the guide structure. The role of guide structure 135 in properly aligning the reload (and hence shuttle contained therein) assists in guiding ramped edge 138 of shuttle 130 into contact with ramped surface 117 of distal portion 119 of locking member 116 so that locking member 116 rides up proximal ramped portion 138 of shuttle 130 and onto shelf 132 as described above.

Figure 20:
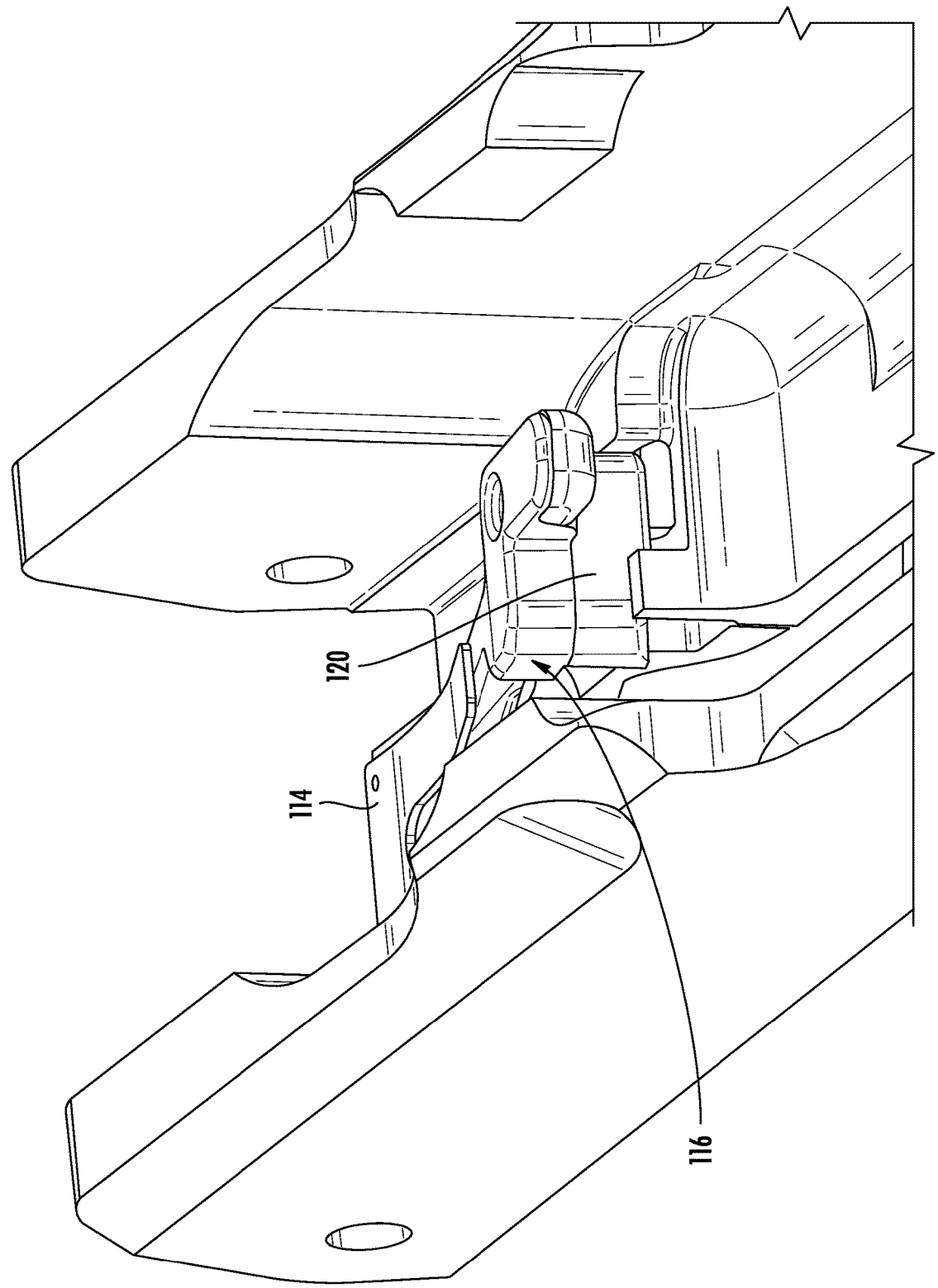
FIG. 20 is a partial perspective view of the distal end of a channel and a locking member in accordance with the embodiment of FIG. 2 illustrating a guard wall of the locking member bottom.

FIG. 20 shows a front wall 120 of locking member 116. Front wall 120 is positioned towards the distal end of locking member 116, as it provides a barrier to protect the rest of locking member 116. It is envisioned that front wall 120 of locking member 116 may prevent a user from accidentally damaging or popping out locking member 116 during cleaning or repair of a surgical stapling instrument in accordance with this disclosure.

Figure 21:
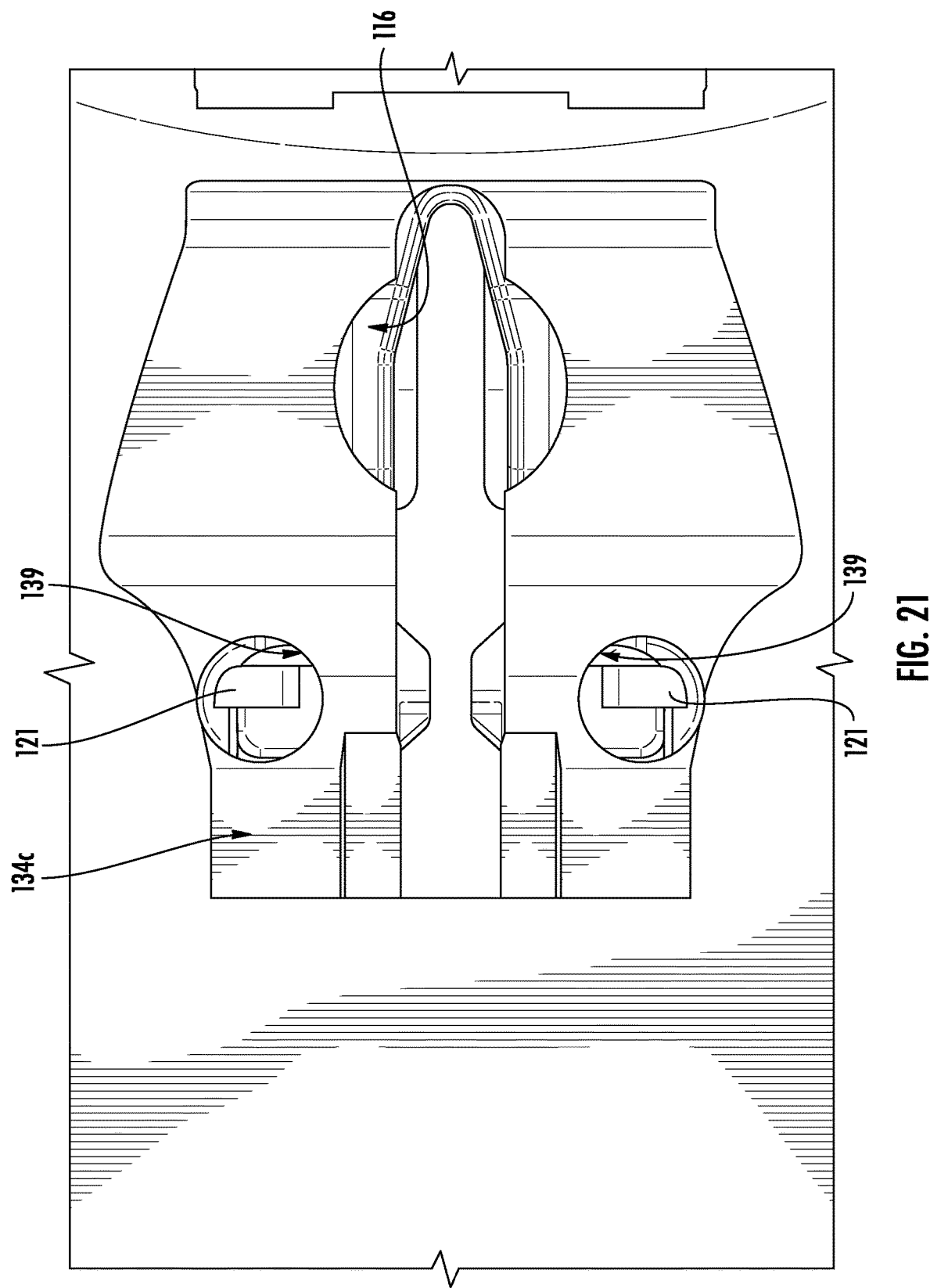
FIG. 21 is a bottom view of the channel of FIG. 20 showing the feet of the locking member positioned through openings in the bottom wall of the channel.

FIG. 21 shows an additional feature of locking member 116. Specifically, FIG. 21 shows a pair of feet 121 configured to pass through openings 139 formed on the bottom wall 134c of channel 134. Feet 121 prevent a user from accidentally removing or repositioning locking member 116. In order to remove locking member 116, a user pinches the pair of feet 121 towards the center of channel 134, and then guide feet 121 up and out through openings 139 of channel 134. Feet 121 allow a user to remove locking member 116 for cleaning if necessary, while also preventing unintentional movement of the locking member when loading, using, or moving a surgical stapling instrument. The distally extending arms 171 can flex to move the feet from the first position to the second position.

Figure 22:
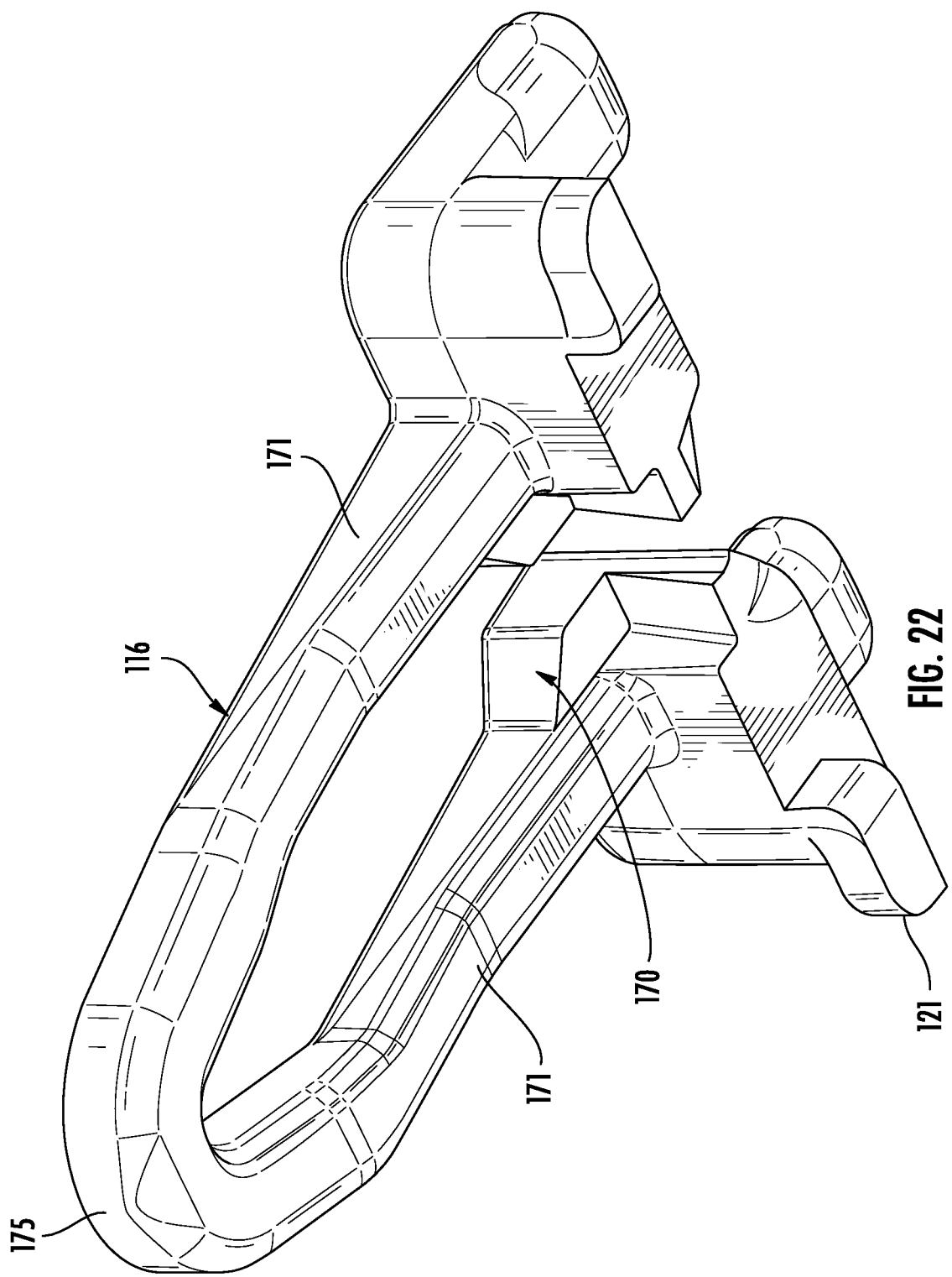
FIG. 22 is a bottom perspective view of a locking member in accordance with the embodiment of FIG. 21.
Figure 23:
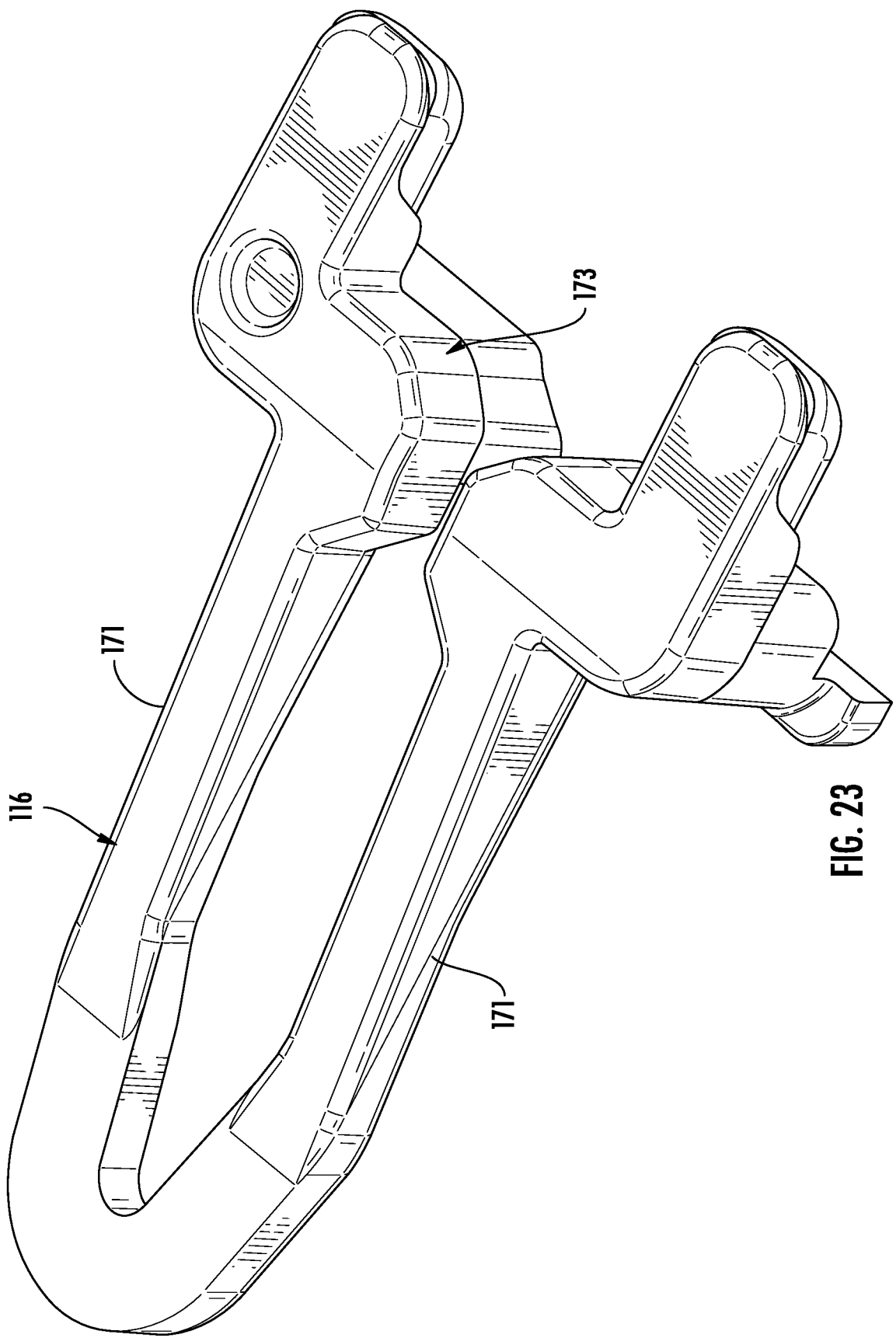
FIG. 23 is a top perspective view of a locking member in accordance with the embodiment of FIG. 21.
Figure 24C:
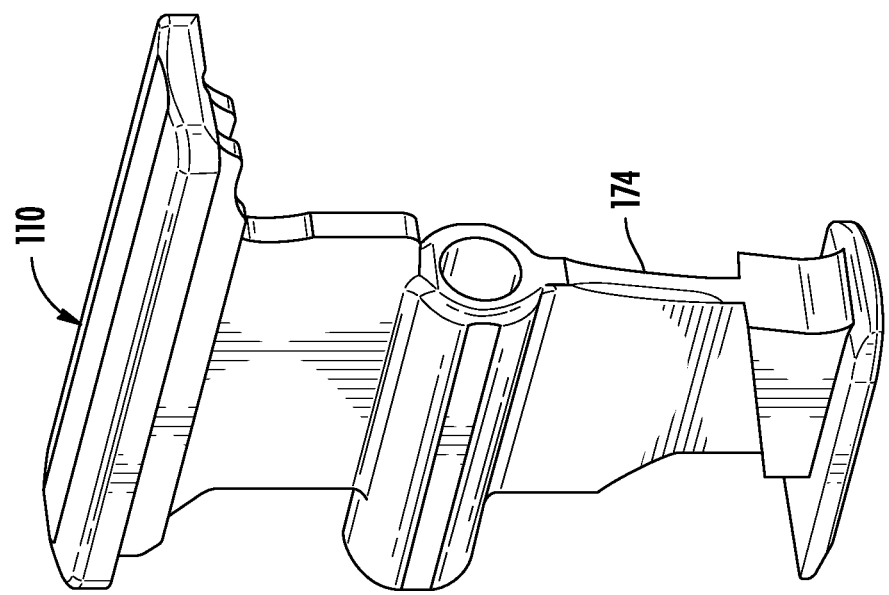
FIGS. 24 A, B, and C are a front, side, and perspective view, respectively, of a drive member of a surgical stapling instrument configured to engage a locking member in accordance with the embodiment of FIGS. 22-23.
Figure 24B:
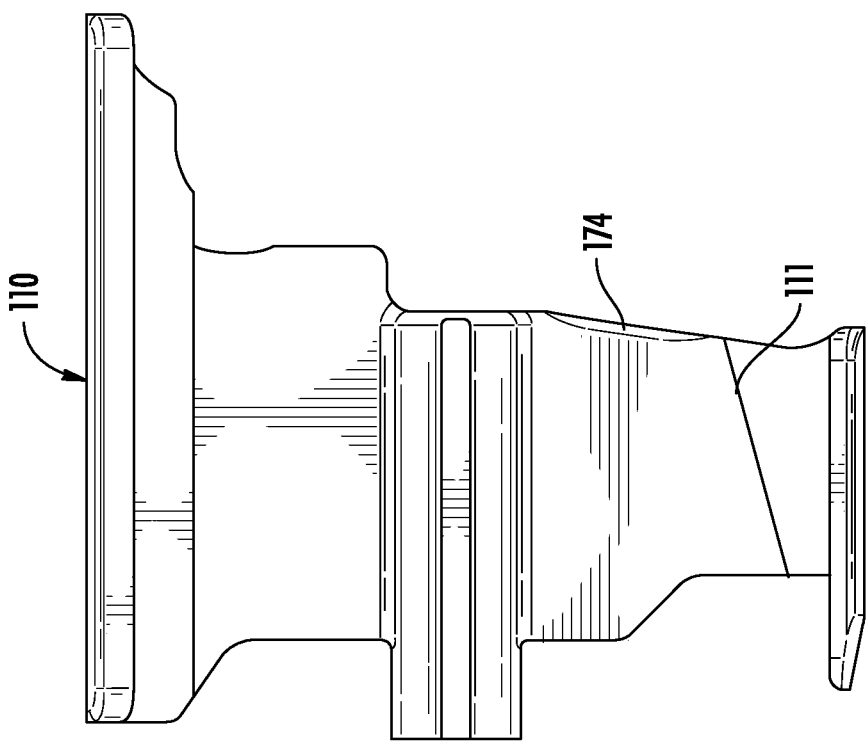
Figure 24A:
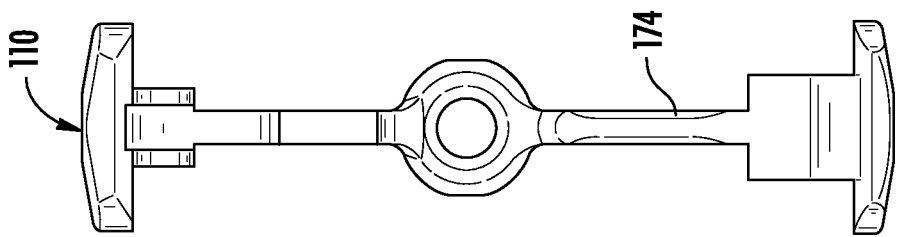
Figure 26:
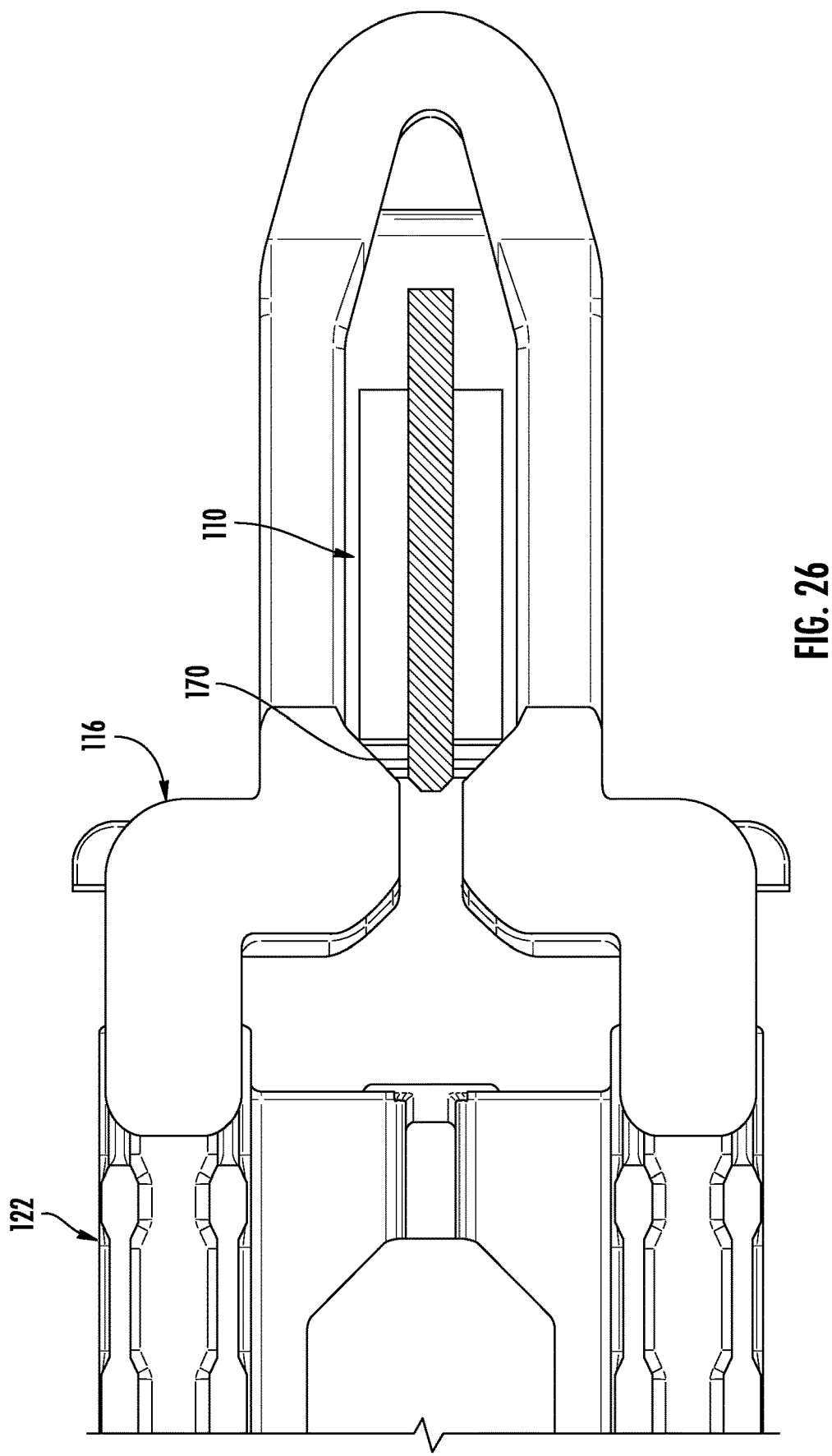
FIG. 26 is a partial top view of FIG. 25.

FIG. 22 shows an illustrative embodiment of locking member 116 in accordance with this disclosure having proximally-facing chamfered surfaces 170 formed on distally extending arms 171 of locking member 116. Locking member 116 may be generally "U-Shaped" with distally extending arms 171 originating for a proximal central portion 175 of locking member 116. Proximally-facing chamfered surfaces 170 are configured to engage and align drive member 110 along the longitudinal axis "A" of channel 134 (See FIG. 17) as drive member 110 translates distally between arms 171 of locking member 116. As best seen in FIG. 23, in embodiments locking member 116 may also have distally-facing chamfered surfaces 173 configured to engage and align drive member 110 along the longitudinal axis of channel 134 as drive member 110 retracts and moves between arms 171 of locking member 116. Chamfered surfaces 170 and 173 together help to prevent the drive member 110 from unintentionally contacting any edges or corners of locking member 116, while also promoting proper alignment during translation of drive member 110. As best seen in FIG. 24, drive member 110 may have a chamfered edge 174 to assist in alignment by surfaces 170 and 173.

While several embodiments of this disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A surgical stapling instrument comprising:
   first and second jaws, wherein one of the first and second jaws comprises a channel configured to receive a staple cartridge, the channel including at least one sidewall and a bottom wall, the bottom wall including at least one opening;
   a drive member configured to translate through at least one of the first and second jaws in a distal direction;
   a locking member pivotable between a first position permitting distal translation of the drive member, and a second position preventing distal translation of the drive member;
   the drive member including a ramped portion configured to cooperate with the locking member and pivot the locking member towards the first position as the drive member is translated proximally; and
   wherein the locking member includes at least one foot configured to engage said at least one opening in the bottom wall of the channel.

2. The surgical stapling instrument of claim 1, further comprising a spring configured to bias the locking member towards the second position.

3. The surgical stapling instrument of claim 1, wherein the staple cartridge includes a shuttle having a shelf, and wherein the locking member is disposed on the shelf when the locking member is in the first position.

4. The surgical stapling instrument of claim 1, wherein the channel further includes a slot, the locking member being configured to engage the slot in the second position.

5. The surgical stapling instrument of claim 1, wherein the at least one side wall includes two side walls and wherein a cam surface is adjacent the bottom wall.

6. The surgical stapling instrument of claim 5, wherein the at least one opening includes a pair of openings and the at least one foot includes a pair of feet configured to pass through respective openings in the bottom wall, the feet being movable from a first position preventing removal of the feet from the openings, to a second position allowing removal of the feet from the openings.

7. The surgical stapling instrument of claim 6, wherein the locking member includes a pair of distally extending arms, the feet formed on the distal portion thereof and wherein the distally extending arms can flex to move the feet from the first position to the second position.

8. The surgical stapling instrument of claim 1, wherein the first jaw is an anvil jaw assembly and the second jaw is a staple jaw assembly and wherein the staple cartridge comprises a shuttle, the drive member being configured to releasably engage and translate the shuttle in the distal direction through a staple firing stroke.

9. The surgical stapling instrument of claim 1, wherein the locking member is generally U-shaped.

10. The surgical instrument of claim 1, wherein the drive member is actuated by a robotic surgical system.

11. A surgical stapling instrument comprising:
    first and second jaws;
    a drive member configured to translate in a distal direction through at least one of the first and second jaws;
    a locking member pivotable between a first position permitting distal translation of the drive member, and a second position preventing distal translation of the drive member, wherein the locking member includes a ramped surface;
    wherein at least one of the first and second jaws includes a channel configured to receive a staple cartridge, the channel including at least one sidewall and a bottom wall, the bottom wall including at least one opening, the staple cartridge including a ramped surface configured to engage the ramped surface of the locking member to maintain the locking member in the first position; and
    wherein the locking member includes at least one foot configured to engage said at least one opening in the bottom wall of the channel.

12. The surgical stapling instrument of claim 11, further comprising a spring configured to bias the locking member towards the second position.

13. The surgical stapling instrument of claim 12, wherein the channel further includes a slot, the locking member being configured to engage the slot in the second position.

14. The surgical stapling instrument of claim 11, wherein the staple cartridge includes a shuttle and the at least one sidewall includes two sidewalls with each sidewall having a guide structure and wherein the ramped surface of the staple cartridge resides on the shuttle.

15. The surgical stapling instrument of claim 14, wherein the guide structure is configured to direct the ramped surface of the shuttle into contact with the ramped surface of the locking member when the drive member is translated in the distal direction.

16. A surgical stapling instrument comprising:
    first and second jaws, at least one of the first and second jaws including a channel defining a longitudinal axis, having at least one side wall and a bottom wall and being configured to receive a staple cartridge, the bottom wall including at least one opening;
    a drive member configured to in a distal direction through at least one of the first and second jaws; and
    a locking member pivotable between a first position permitting distal translation of the drive member, and a second position preventing distal translation of the drive member, the locking member including a pair of arms, each arm having a surface configured to engage and align the drive member along the longitudinal axis of the channel as the drive member translates distally between the arms of the locking member, and
    wherein the locking member includes at least one foot configured to engage said at least one opening in the bottom wall of the channel.

17. The surgical stapling instrument of claim 16, wherein the locking member further includes a pair of distally facing chamfered surfaces.

18. The surgical stapling instrument of claim 16, wherein the locking member is generally U-shaped.

19. The surgical instrument of claim 16, wherein the pair of arms extend distally from the locking member and wherein the surface of each arm is a proximally facing chamfered surface.

20. The surgical stapling instrument of claim 16, wherein the staple cartridge includes a shuttle, and wherein the drive member is configured to releasably engage and translate the shuttle in the distal direction through a staple firing stroke.

* * * * *